(12) United States Patent

Corbett et al.

(10) Patent No.: US 12,558,040 B2

(45) Date of Patent: Feb. 24, 2026

(54) USING AN ONLINE DISTURBANCE REJECTION AND ANTICIPATION SYSTEM TO REDUCE HYPERGLYCEMIA

(71) Applicant: University of Virginia Patent Foundation, Charlottesville, VA (US)

(72) Inventors: John P. Corbett, San Diego, CA (US); Jose Garcia-Tirado, Earlysville, VA (US); Patricio Colmegna, Charlottesville, VA (US); Jenny L Diaz-Castañeda, Charlottesville, VA (US); Marc D. Breton, Charlottesville, VA (US)

(73) Assignee: UNIVERSITY OF VIRGINIA PATENT FOUNDATION

( * ) Notice: Subject to any disclaimer, the term of this patent is extended or adjusted under 35 U.S.C. 154(b) by 784 days.

(21) Appl. No.: 17/932,496

(22) Filed: Sep. 15, 2022

(65) Prior Publication Data

US 2023/0097161 A1 Mar. 30, 2023

Related U.S. Application Data

(60) Provisional application No. 63/244,368, filed on Sep. 15, 2021.

(51) Int. Cl.

| *A61B 5/00* | (2006.01) |
| *A61B 5/11* | (2006.01) |

(Continued)

(52) U.S. Cl.

CPC .......... *A61B 5/7275* (2013.01); *A61B 5/1118* (2013.01); *A61B 5/14532* (2013.01);

(Continued)

(58) Field of Classification Search

None

See application file for complete search history.

(56) References Cited

U.S. PATENT DOCUMENTS

| 2013/0085772 A1* | 4/2013 | Gaweda | ................. G16H 20/10 |
| | | | 705/2 |
| 2021/0183491 A1 | 6/2021 | Grosman et al. | |

FOREIGN PATENT DOCUMENTS

| WO | WO-2021205479 A2 * | 10/2021 | ............. G06Q 10/04 |

OTHER PUBLICATIONS

Jose Garcia-Tirado et al., Advanced Closed-Loop Control System Improves Postprandial Glycemic Control Compared With a Hybrid Closed-Loop, Diabetes Care 2021;44:2379-2387; https://doi.org/10.2337/dc21-0932. (Year: 2021).*

(Continued)

*Primary Examiner* — Manuel A Mendez

(74) *Attorney, Agent, or Firm* — Buchanan Ingersoll & Rooney PC

(57) ABSTRACT

Embodiments relate to systems and methods for informing, determining, or controlling insulin dosage. The method involves generating plural disturbance profiles, each disturbance profile being a data representation based on historical patient data pertaining to a deviation from a threshold blood glucose level. The method involves receiving current patient data. The method involves applying a predictive model so that current patient data is compared to a disturbance profile and a probability analysis is used to assess the likelihood of a disturbance profile being an anticipated disturbance profile, the anticipated disturbance profile being a disturbance profile that is determined to match with the current patient data based on the probability analysis. The method involves determining an insulin dose amount based on the anticipated disturbance profile. The method involves outputting a signal (Continued)

representative of the insulin dose amount to a device configured for monitoring, influencing, and/or administering insulin levels in the patient.

22 Claims, 11 Drawing Sheets

(51) Int. Cl.
    *A61B 5/145*       (2006.01)
    *G16H 20/17*      (2018.01)
(52) U.S. Cl.
    CPC .......... *A61B 5/4839* (2013.01); *A61B 5/4866*
          (2013.01); *G16H 20/17* (2018.01)

(56) References Cited

OTHER PUBLICATIONS

Jose Garcia-Tirado et al., Advanced hybrid artificial pancreas system improves on unannounced meal response—In silico comparison to currently available system, Computer Methods and Programs in Biomedicine 211 (2021) 106401. (Year: 2021).*

International Search Report and Written Opinion of the International Searching Authority (Forms PCT/ISA/220, PCT/ISA/210 and PCT/ISA/237) issued on Jan. 9, 2023, by the European Patent Office in corresponding International Application No. PCT/US2022/043651. (12 pages).

J. Garcia-Tirado et al., "Advanced Hybrid Artificial Pancreas System Improves on Unannounced Meal Response—In Silico Comparison to Currently Available System", Computer Methods and Programs in Biomedicine, 2021, vol. 211. (9 pages).

Bailey, et al., "Breaking Up Prolonged Sitting with Light-Intensity Walking Improves Postprandial Glycemia, but Breaking Up Sitting with Standing does not", Journal of Science and Medicine in Sport, vol. 18, No. 3, May 1, 2015, pp. 294-298.

Balducci, et al., "Exercise Training Can Modify the Natural History of Diabetic Peripheral Neuropathy", Journal of Diabetes and its Complications, vol. 20, No. 4, Jul.-Aug. 2006, pp. 216-223.

Blauw, et al., "Fully Closed Loop Glucose Control with a Bihormonal Artificial Pancreas in Adults With Type 1 Diabetes: An Outpatient, Randomized, Crossover Trial", Diabetes Care, vol. 44, No. 3, Mar. 2021, pp. 836-838.

Bohn, et al., "Impact of Physical Activity on Glycemic Control and Prevalence of Cardiovascular Risk Factors in Adults With Type 1 Diabetes: A Cross-sectional Multicenter Study of 18,028 Patients", Diabetes Care, vol. 38, No. 8, Aug. 2015, pp. 1536-1543.

Brazeau, et al., "Barriers to Physical Activity Among Patients with Type 1 Diabetes", Diabetes Care, vol. 31, No. 11, Nov. 2008, pp. 2108-2109.

Breton, et al., "Adding Heart Rate Signal to a Control-to-Range Artificial Pancreas System Improves the Protection Against Hypoglycemia During Exercise in Type 1 Diabetes", Diabetes Technology & Therapeutics, vol. 16, No. 8, Aug. 1, 2014, pp. 506-511.

Brown, et al., "Six-Month Randomized, Multicenter Trial of Closed-Loop Control in Type 1 Diabetes", The New England Journal of Medicine, vol. 381, No. 18, Oct. 31, 2019, pp. 1707-1717.

Caliński, et al., "A Dendrite Method for Cluster Analysis", Communications in Statistics, vol. 3, No. 1, 1974, pp. 1-27.

Cappon, et al., "In Silico Assessment of Literature Insulin Bolus Calculation Methods Accounting for Glucose Rate of Change", Journal of Diabetes Science and Technology, vol. 13, No. 1, Jan. 2019, pp. 103-110.

Cinar, Ali, "Multivariable Adaptive Artificial Pancreas System in Type 1 Diabetes", Current Diabetes Reports, vol. 17, Article No. 88, 2017, pp. 1-11.

Colberg, et al., "Physical Activity/Exercise and Diabetes: A Position Statement of the American Diabetes Association", Diabetes Care, vol. 39, No. 11, Nov. 2016, pp. 2065-2079.

Corbett, et al., "Anticipating Meals with Behavioral Profiles in an Artificial Pancreas System—An Informed Multistage Model Predictive Control Approach", IFAC—PapersOnLine, vol. 53, No. 2, 2020, pp. 16305-16310.

Davey, et al., "The Effect of Midday Moderate-Intensity Exercise on Postexercise Hypoglycemia Risk in Individuals With Type 1 Diabetes", The Journal of Clinical Endocrinology & Metabolism, vol. 98, No. 7, Jul. 1, 2013, pp. 2908-2914.

Deboer, et al., "Heart Rate Informed Artificial Pancreas System Enhances Glycemic Control During Exercise in Adolescents with T1D", Pediatric Diabetes, vol. 18, No. 7, 2017, pp. 540-546.

Dovc, et al., "Faster Compared with Standard Insulin Aspart During Day-and-Night Fully Closed-Loop Insulin Therapy in Type 1 Diabetes: A Double-Blind Randomized Crossover Trial", Diabetes Care, vol. 43, No. 1, Jan. 2020, pp. 29-36.

Dunstan, et al., "Breaking Up Prolonged Sitting Reduces Postprandial Glucose and Insulin Responses", Diabetes Care, vol. 35, No. 5, May 2012, pp. 976-983.

Ellingsen, et al., "Safety Constraints in an Artificial Pancreatic B Cell: An Implementation of Model Predictive Control with Insulin on Board", Journal of Diabetes Science and Technology, vol. 3, Issue 3, May 2009, pp. 536-544.

Forlenza, et al., "Fully Closed-Loop Multiple Model Probabilistic Predictive Controller Artificial Pancreas Performance in Adolescents and Adults in a Supervised Hotel Setting", Diabetes Technology & Therapeutics, vol. 20, No. 5, May 1, 2018, pp. 335-343.

Garcia-Tirado, et al., "Anticipation of Historical Exercise Patterns by a Novel Artificial Pancreas System Reduces Hypoglycemia During and After Moderate-Intensity Physical Activity in People with Type 1 Diabetes", Diabetes Technology & Therapeutics, vol. 23, No. 4, Apr. 2021, pp. 277-285.

Garcia-Tirado, et al., "Closed-Loop Control with Unannounced Exercise for Adults with Type 1 Diabetes using the Ensemble Model Predictive Control", Journal of Process Control, vol. 80, Aug. 2019, pp. 202-210.

Garcia-Tirado, et al., "Ensemble Model Predictive Control Strategies Can Reduce Exercise Hypoglycemia in Type 1 Diabetes: In Silico Studies", American Control Conference (ACC), Jul. 10-12, 2019, pp. 4752-4758.

Garcia-Tirado, et al., "In Silico Analysis of an Exercise-Safe Artificial Pancreas with Multistage Model Predictive Control and Insulin Safety System", Journal of Diabetes Science and Technology, vol. 13, No. 6, Nov. 2019, pp. 1054-1064.

Gingras, et al., "The Challenges of Achieving Postprandial Glucose Control using Closed-Loop Systems in Patients with Type 1 Diabetes", Diabetes, Obesity & Metabolism, vol. 20, No. 2, Feb. 2018, pp. 245-256.

Haidar, et al., "Reducing the need for Carbohydrate Counting in Type 1 Diabetes Using Closed-Loop Automated Insulin Delivery (Artificial Pancreas) and Empagliflozin: A Randomized, Controlled, Non-Inferiority, Crossover Pilot Trial", Diabetes, Obesity and Metabolism, vol. 23, 2021, pp. 1272-1281.

Hamming, R. W., "Error Detecting and Error Correcting Codes", The Bell System Technical Journal, vol. 29, No. 2, Apr. 1950, pp. 147-160.

Harvey, et al., "Clinical Evaluation of an Automated Artificial Pancreas Using Zone-Model Predictive Control and Health Monitoring System", Diabetes Technology & Therapeutics, vol. 16, No. 6, Jun. 1, 2014, pp. 348-357.

Lloyd, Stuart P, "Least Squares Quantization in PCM", IEEE Transactions on Information Theory, vol. 28, No. 2, Mar. 1982, pp. 129-137.

Maahs, et al., "Outcome Measures for Artificial Pancreas Clinical Trials: A Consensus Report", Diabetes Care, vol. 39, No. 7, Jul. 2016, pp. 1175-1179.

Majdpour, et al., "Fully Automated Artificial Pancreas for Adults With Type 1 Diabetes Using Multiple Hormones: Exploratory Experiments", Canadian Journal of Diabetes, vol. 45, No. 8, Dec. 1, 2021, pp. 734-742 (9 pages).

Manohar, et al., "The Effect of Walking on Postprandial Glycemic Excursion in Patients With Type 1 Diabetes and Healthy People", Diabetes Care, vol. 35, No. 12, Dec. 2012, pp. 2493-2499.

(56) References Cited

OTHER PUBLICATIONS

Mcmahon , et al., "Glucose Requirements to Maintain Euglycemia After Moderate-Intensity Afternoon Exercise in Adolescents With Type 1 Diabetes Are Increased in a Biphasic Manner", J Clin Endocrinol Metab., vol. 92, No. 3, 2007, pp. 963-968.

Ozaslan , et al., "Automatically Accounting for Physical Activity in Insulin Dosing for Type 1 Diabetes", Computer Methods and Programs in Biomedicine, vol. 197, Dec. 2020, pp. 1-15.

Ozaslan , et al., "Impact of Daily Physical Activity as Measured by Commonly Available Wearables on Mealtime Glucose Control in Type 1 Diabetes", Diabetes Technology & Therapeutics, vol. 22, No. 10, Oct. 2020, pp. 742-748.

Ozaslan , et al., "Safety and Feasibility Evaluation of Step Count Informed Meal Boluses in Type 1 Diabetes: A Pilot Study", Journal of Diabetes Science and Technology, vol. 16, No. 3, May 2022, pp. 670-676.

Paffenbarger , et al., "Physical Activity, All-Cause Mortality, And Longevity of College Alumni", The New England Journal of Medicine, vol. 314, No. 10, Mar. 6, 1986, pp. 605-613.

Patek, Stephen D, "Open-Loop Feedback Control Under Multiple Disturbance Function Hypotheses", 49th IEEE Conference on Decision and Control, Dec. 15-17, 2010, pp. 4165-4170.

Peddie , et al., "Breaking Prolonged Sitting Reduces Postprandial Glycemia in Healthy, Normal-Weight Adults: A Randomized Crossover Trial", American Journal of Clinical Nutrition, vol. 98, No. 2, Aug. 2013, pp. 358-366.

Riddell , et al., "Exercise and the Development of the Artificial Pancreas: One of the More Difficult Series of Hurdles", Journal of Diabetes Science and Technology, vol. 9, No. 6, Nov. 2015, pp. 1217-1226.

Riddell , et al., "Exercise Management in Type 1 Diabetes: A Consensus Statement", The Lancet Diabetes and Endocrinology, vol. 5, No. 5, May 1, 2017, pp. 377-390.

Swan , et al., "Effect of Age of Infusion Site and Type of Rapid-Acting Analog on Pharmacodynamic Parameters of Insulin Boluses in Youth With Type 1 Diabetes Receiving Insulin Pump Therapy", Diabetes Care, vol. 32, No. 2, Feb. 2009, pp. 240-244.

Turksoy , et al., "Multivariable Adaptive Closed-Loop Control of an Artificial Pancreas Without Meal and Activity Announcement", Diabetes Technology & Therapeutics, vol. 15, No. 5, May 2013, pp. 386-400.

Msentin , et al., "The UVA/Padova Type 1 Diabetes Simulator Goes from Single Meal to Single Day", Journal of Diabetes Science and Technology, vol. 12, No. 2, Mar. 2018, pp. 273-281.

Warburton , et al., "Health Benefits of Physical Activity: The Evidence", CMAJ : Canadian Medical Association Journal, vol. 174, No. 6, Mar. 14, 2006, pp. 801-809 (24 pages).

White , et al., "Ecologists Should not use Statistical Significance Tests to Interpret Simulation Model Results", Oikos, vol. 123, No. 4, Apr. 2014, pp. 385-388.

Office Action issued on Mar. 11, 2025, by the Canadian Patent Office in corresponding Canadian Patent Application No. 3,231,797. (4 pages).

* cited by examiner

System 1000

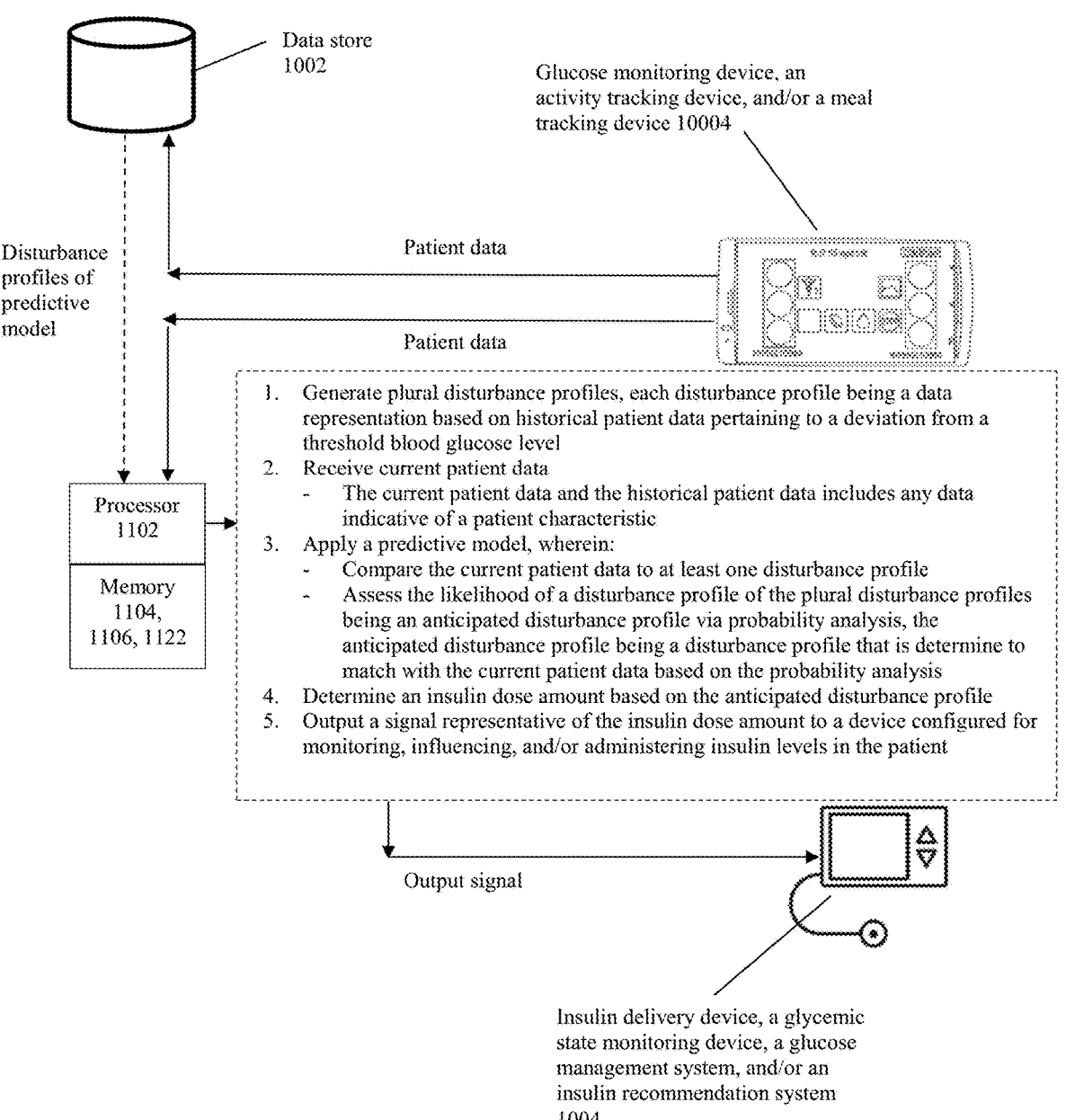

Data store
1002

Glucose monitoring device, an
activity tracking device, and/or a meal
tracking device 10004

Disturbance
profiles of
predictive
model

Patient data

Patient data

Processor
1102

Memory
1104,
1106, 1122

1. Generate plural disturbance profiles, each disturbance profile being a data
   representation based on historical patient data pertaining to a deviation from a
   threshold blood glucose level
2. Receive current patient data
   - The current patient data and the historical patient data includes any data
     indicative of a patient characteristic
3. Apply a predictive model, wherein:
   - Compare the current patient data to at least one disturbance profile
   - Assess the likelihood of a disturbance profile of the plural disturbance profiles
     being an anticipated disturbance profile via probability analysis, the
     anticipated disturbance profile being a disturbance profile that is determine to
     match with the current patient data based on the probability analysis
4. Determine an insulin dose amount based on the anticipated disturbance profile
5. Output a signal representative of the insulin dose amount to a device configured for
   monitoring, influencing, and/or administering insulin levels in the patient Output signal Insulin delivery device, a glycemic
state monitoring device, a glucose
management system, and/or an
insulin recommendation system
1004

FIG. 1

USING AN ONLINE DISTURBANCE REJECTION AND ANTICIPATION SYSTEM TO REDUCE HYPERGLYCEMIA

CROSS-REFERENCE TO RELATED APPLICATIONS

This patent application is related to and claims the benefit of priority of U.S. Provisional Application No. 63/244,368, filed on Sep. 15, 2021, the entire contents of which is incorporated by reference.

FIELD

Embodiments relate to systems and methods of for informing, determining, or controlling insulin dosage based on disturbance profiles associated with patterns of blood glucose level disturbances causes by physical activity, meal activity, etc.

BACKGROUND INFORMATION

Preventing hyperglycemia following eating, exercise, etc. is still a persistent issue for people with type 1 diabetes (T1D), even while using conventional an automated insulin dosing system (AID) which delivers insulin variably based on an internal closed-loop algorithm. The unwanted increase in plasma blood glucose (BG) following eating, exercise, etc. for people with T1D is primarily a result of the dynamics associated with subcutaneously injected insulin, ingested carbohydrates, exercise, etc. Currently available subcutaneous insulin analogs have slower time constants than consumed carbohydrates, thus necessitating the use of feedforward control to prevent hyperglycemia. Anticipation and automatic bolusing in an advanced control system framework have proven to compensate for the inherent absorption delay from current insulin analogs; yet, such systems can be improved.

SUMMARY

An exemplary embodiment relates to a system for informing, determining, or controlling insulin dosage. The system can include a processor. The system can include memory including instructions to cause the processor to execute functions associated with embodiments of the method disclosed herein. The instructions can cause the processor to generate plural disturbance profiles, each disturbance profile being a data representation based on historical patient data pertaining to a deviation from a threshold blood glucose level. The instructions can cause the processor to receive current patient data. The current patient data and the historical patient data includes any data indicative of a patient characteristic. The instructions can cause the processor to apply a predictive model. The processor is configured by the instructions to compare the current patient data to at least one disturbance profile. The processor is configured by the instructions to assess the likelihood of a disturbance profile of the plural disturbance profiles being an anticipated disturbance profile via probability analysis, the anticipated disturbance profile being a disturbance profile that is determine to match with the current patient data based on the probability analysis. The instructions can cause the processor to determine an insulin dose amount based on the anticipated disturbance profile. The instructions can cause the processor to output a signal representative of the insulin dose amount to a device configured for monitoring, influencing, and/or administering insulin levels in the patient.

An exemplary embodiment relates to a computer readable medium having instructions stored thereon that when executed by a processor causes the processor to execute functions associated with embodiments of the method disclosed herein. The instructions can cause the processor to generate plural disturbance profiles, each disturbance profile being a data representation based on historical patient data pertaining to a deviation from a threshold blood glucose level. The instructions can cause the processor to receive current patient data. The current patient data and the historical patient data includes any data indicative of a patient characteristic. The instructions can cause the processor to apply a predictive model. The processor is configured by the instructions to compare the current patient data to at least one disturbance profile. The processor is configured by the instructions to assess the likelihood of a disturbance profile of the plural disturbance profiles being an anticipated disturbance profile via probability analysis, the anticipated disturbance profile being a disturbance profile that is determine to match with the current patient data based on the probability analysis. The instructions can cause the processor to determine an insulin dose amount based on the anticipated disturbance profile. The instructions can cause the processor to output a signal representative of the insulin dose amount to a device configured for monitoring, influencing, and/or administering insulin levels in the patient.

An exemplary embodiment relates to a method for informing, determining, or controlling insulin dosage. The method involves generating plural disturbance profiles, each disturbance profile being a data representation based on historical patient data pertaining to a deviation from a threshold blood glucose level. The method involves receiving current patient data. The current patient data and the historical patient data includes any data indicative of a patient characteristic. The method involves applying a predictive model in which the current patient data is compared to at least one disturbance profile, and probability analysis is used to assess the likelihood of a disturbance profile of the plural disturbance profiles being an anticipated disturbance profile, the anticipated disturbance profile being a disturbance profile that is determined to match with the current patient data based on the probability analysis. The method involves determining an insulin dose amount based on the anticipated disturbance profile. The method involves outputting a signal representative of the insulin dose amount to a device configured for monitoring, influencing, and/or administering insulin levels in the patient.

BRIEF DESCRIPTION OF THE DRAWINGS

Other features and advantages of the present disclosure will become more apparent upon reading the following detailed description in conjunction with the accompanying drawings, wherein like elements are designated by like numerals, and wherein:

FIG. 1 shows an exemplary system architecture for implementing an embodiment of the method;

DETAILED DESCRIPTION

Figure 11:
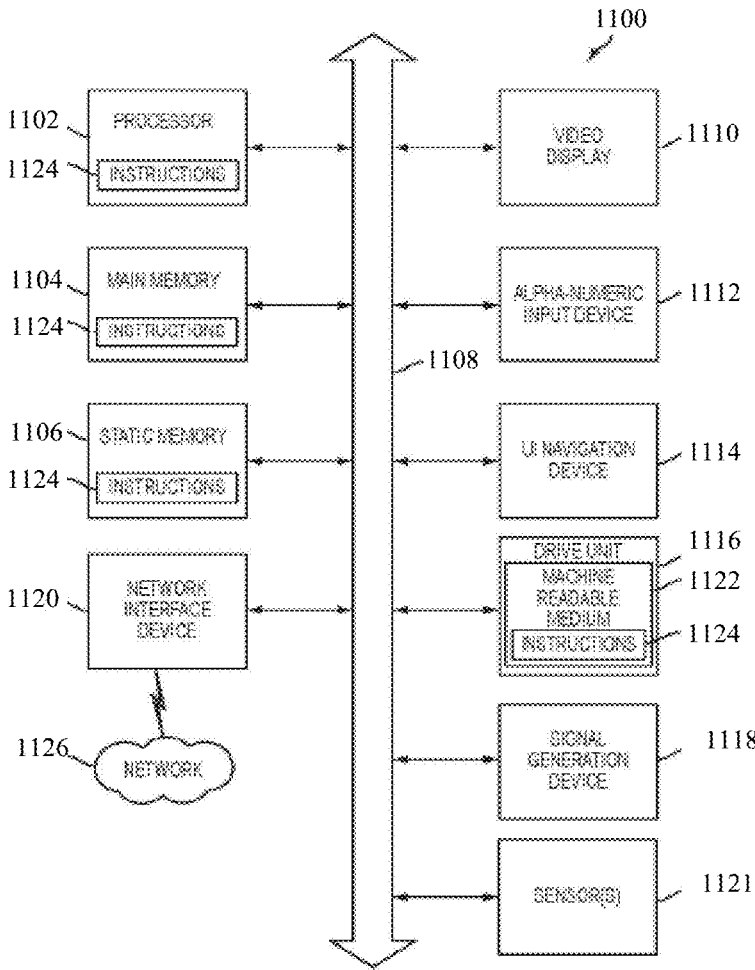
FIG. 11 shows a block diagram illustrating an example of a machine upon which one or more aspects of embodiments of the present invention can be implemented.

Referring to FIGS. 1 and 11, embodiments can relate to a system 1000 for informing, determining, or controlling insulin dosage. The system 1000 can include a processor 1102 configured to build and/or implement a predictive model. The system can include memory 1104, 1106, 1122 having instruction to cause the processor 1102 to execute any of the method steps disclosed herein. The processor 1102 can be any of the processors 1102 disclosed herein. The processor 1102 can be part of or in communication with a machine 1100 (logic, one or more components, circuits (e.g., modules), or mechanisms). The processor 1102 can be hardware (e.g., processor, integrated circuit, central processing unit, microprocessor, core processor, computer device, etc.), firmware, software, etc. configured to perform operations by execution of instructions embodied in algorithms, data processing program logic, artificial intelligence programming, automated reasoning programming, etc. It should be noted that use of processors 1102 herein includes any one or combination of a Graphics Processing Unit (GPU), a Field Programmable Gate Array (FPGA), a Central Processing Unit (CPU), etc. The processor 1102 can include one or more processing modules. A processing module can be a software or firmware operating module configured to implement any of the method steps disclosed herein. The processing module can be embodied as software and stored in memory, the memory being operatively associated with the processor 1102. A processing module can be embodied as a web application, a desktop application, a console application, etc. Exemplary embodiments of the processor 1102 and the machine 1100 are discussed later.

The processor 1102 can include or be associated with a computer or machine readable medium 1122. As discussed in more detail later, the computer or machine readable medium 1122 can include memory. Any of the memory discussed herein can be computer readable memory configured to store data. The memory can include a volatile or non-volatile, transitory or non-transitory memory, and be embodied as an in-memory, an active memory, a cloud memory, etc. Embodiments of the memory can include a processor module and other circuitry to allow for the transfer of data to and from the memory, which can include to and from other components of a communication system. This transfer can be via hardwire or wireless transmission. The communication system can include transceivers, which can be used in combination with switches, receivers, transmitters, routers, gateways, wave-guides, etc. to facilitate communications via a communication approach or protocol for controlled and coordinated signal transmission and processing to any other component or combination of components of the communication system. The transmission can be via a communication link. The communication link can be electronic-based, optical-based, opto-electronic-based, quantum-based, etc.

The computer or machine readable medium 1122 can be configured to store one or more instructions 1124 thereon. The instructions 1124 can be in the form of algorithms, program logic, etc. that cause the processor 1102 to build and/or implement a predictive model.

The processor 1102 can be in communication with other processors of other devices 1004 (e.g., a glycemic state monitoring device, a glucose management system, an insulin recommendation system, an insulin delivery device, a glucose monitoring device, an activity tracking device, a meal tracking device, etc.). Any of those other devices 1004 can include any of the exemplary processors 1102 disclosed herein. Any of the processors can have transceivers or other communication devices/circuitry to facilitate transmission and reception of wireless signals. Any of the processors can include an Application Programming Interface (API) as a software intermediary that allows two applications to talk to each other. Use of an API can allow software of the processor 1102 of the system 1000 to communicate with software of the processor of the other device(s) 1004.

In some embodiments, the processor 1102 is configured to build the predictive model. In some embodiments, the processor 1102 is configured to implement the predictive model (e.g., the predictive model being already constructed via another processor and stored in memory (e.g., memory 1104, 1106, 1122, data store 1002, etc.) associated with or accessible to the processor 1102). In some embodiments, the processor 1102 is configured to build and implement the predictive model.

As will be explained in more detail later, embodiments of the predictive model can be applied to disturbance profiles to assess a likelihood that any one or combination of the disturbance profiles is an anticipation disturbance profile, the anticipation disturbance profile being a disturbance profile that closely matches with current patient data so as to anticipate a disturbance in the patient's blood glucose levels. In some embodiments, the processor 1102 is configured to generate the disturbance profiles. In some embodiments, the processor 1102 is configured to implement the predictive model using disturbance profiles already constructed via another processor and stored in the memory (e.g., memory 1104, 1106, 1122, data store 1002, etc.) associated with or accessible to the processor 1102. In some embodiments, the processor 1102 is configured to generate disturbance profiles and use disturbance profiles already constructed. The disturbance profiles are based on historical patient data, but can also be updated via the current patient data.

In an exemplary embodiment, the instructions 1124 can cause the processor 1102 to generate at least one disturbance profile. Each disturbance profile can be a data representation based on historical patient data pertaining to a deviation from a threshold blood glucose level. For instance, historical patient data can be analyzed to determine that on certain days, certain times of a day, etc. the patient does something that creates a "disturbance" that causes a deviation in the patient's "normal" or average blood glucose levels. For example, people (and more so those with (T1D)) tend to adhere to a schedule or at least exhibit habitual behavior—e.g., they eat at certain times, exercise at certain days/times, etc. Eating and physical activity can cause fluctuations in blood glucose levels, but due to the habitual nature of when this occurs these fluctuations can be part of the "norm." However, an analysis can be performed to determine that a patient eats early on Fridays 30% of the time, for example.

As another example, while a patient may exercise Saturday mornings, this physical activity may occur at 9:00 AM 80% of the time, 10:00 AM 15% of the time, and 5% of the time skips the exercise. Based on this historical data analysis (this will be explained in detail later), disturbance profiles can be generated to capture these disturbances. Threshold(s) can be set to determine what constitutes a disturbance. A threshold may be set based on the patient's average blood glucose level, a range of blood glucose levels (e.g., bands set by standard deviations about a mean average), an expected blood glucose level, a desired blood glucose level, etc. These can be overall averages/ranges/expected/desired levels for the time period of historical data, averages/ranges/expected/desired levels for a given day, averages/ranges/expected/desired levels for a given time of day, etc. The threshold(s) can be set such that the deviation from the threshold blood glucose level for the disturbance profile is an occurrence of a blood glucose level caused by physical activity, meal activity, etc. that increases a risk of hyperglycemia and/or hypoglycemia. The physical activity, meal activity, etc. that increases a risk of hyperglycemia and/or hypoglycemia can be identified via state of the art fault detection or classification techniques, for example logistical regression or artificial neural networks. As a non-limiting example, the physical activity, meal activity, etc. can include physical activity, meal activity, etc. exhibited by the patient that deviates from a threshold that is an average behavior related to physical activity, meal activity, etc.

While exemplary embodiments discuss use an analysis of blood glucose levels or blood glucose measurements, it is understood that other levels/measurements (e.g., interstitial glucose) can be used/analyzed in addition to or in the alternative to blood glucose.

Clustering techniques (e.g., k-means with hamming distance) can be used to determine which days, times, activities should be grouped together to form a disturbance profile. An exemplary implementation of clustering is discussed in detail later. It is contemplated for more than one disturbance profile to be generated. While clustering techniques can be used to determine which days, times, activities should be grouped together to form a disturbance profile, it is understood that a disturbance profile can be bound to a day (e.g., just for Fridays), bound to a certain activity (e.g., just for eating), bound to a certain activity that occurs early, etc. As a non-limiting example, historical patient data can include data that pertains to more than one day, and clustering can be used to group days having similar deviations from threshold blood glucose levels. For instance, the clustering technique can cluster days so as to determine, for instance, every Friday at 4:00 PM there is a particular disturbance due to a particular type of activity.

Each disturbance profile can be a data representation (e.g., a graph, a trendline, a polynomial function, a data array, etc.) of the historical data that mathematically models the disturbance. The data representation for any one or combination of disturbance profiles can be stored in memory.

The instructions 1124 can cause the processor 1102 to receive current patient data. Current patient data and/or the historical patient data can include any data indicative of a patient characteristic (e.g., data that provides information about a patient's metabolic state, glycemic state, meal activity, physical activity, insulin on board, etc.). Examples of current patient data and/or historical patient data can be glucose measurements, meal intake data, physical activity measurements, insulin injection data, etc. Historical patient data can be data that has already influenced or contributed to a disturbance, which can include baseline data. Current patient data can be data that: 1) is/can/may influencing or contributing to; 2) is/can/may about to influence or contribute to; and/or 3) is/can/may expected to influence or contribute to a disturbance. For instance, current patient data can data received within the past 24 hours or less.

The instructions 1124 can cause the processor 1102 to apply a predictive model. Details of the predictive model will be explained later, but the predictive model can be used to determine the likelihood that a patient is entering/experiencing or about to enter/experience a disturbance based on the current patent data being received. For instance, the processor 1102 can be configured by the instructions 1124 to compare the current patient data to at least one disturbance profile. This comparison can occur continuously, periodically, at a predetermined time, etc. For instance, the current patient data can be generated and/or received continuously, periodically, at a predetermined time, etc., wherein the processor 1102 makes the comparison as soon as the data is generated and/or received. As another example, the current patient data can be stored in memory after it is generated, wherein the processor 1102 pulls the data from memory continuously, periodically, at a predetermined time, etc. and makes the comparison. As a non-limiting example discussed in more detail herein, the processor 1102 is configured by the instructions 1124 to compare the current patient data to at least one disturbance profile every five minutes.

The processor 1102 can be configured by the instructions 1124 to assess the likelihood of a disturbance profile of the plural disturbance profiles being an anticipated disturbance profile. This assessment can be via probability analysis. An anticipated disturbance profile is a disturbance profile that is determine to match (the matching procedure can use any state of the art distance measures between two set of data, e.g. the minimum $L^2$ distance between the linearly transformed disturbance profile and the data, a.k.a linear regression) with the current patient data based on the probability analysis. There can be a match with more than one disturbance profile—e.g., there can be more than one anticipated disturbance profile. A threshold(s) can be set for determining what constitutes a match. A threshold for determining a match between current patient data and one disturbance profile can be the same or different for a threshold for determining a match between current patient data and another disturbance profile. Furthermore, current patient data can be segmented (e.g., into physical activity data, into meal data, into past one-hour increments data, etc.), wherein one segment of current patient data can be compared using a threshold that is the same or different for another segment of current patient data.

The processor 1102 can be configured by the instructions 1124 to determine an insulin dose amount based on the anticipated disturbance profile. This determination of an insulin dose can be via a cost function, objective function, loss function, etc. In some embodiments, the determination can be based on the best match to one or more disturbance profiles. In some embodiments, the determination can be based on a weighting factor assigned to one or more disturbance profiles, one or more weighting factors assigned to one or more disturbance profiles, etc. For instance, in a non-limiting example, the current patent data can be compared to the disturbance profiles, and a weighting factor can be assigned to a disturbance profile based on the comparison. A disturbance profile can be assigned a weighting factor based on the assessed likelihood it is an anticipated disturbance profile—e.g., it is assigned a weighting factor based on how well it matches with the current patent data. A weighting factor can be assigned to any one or combination of disturbance profiles. Any one or combination of weighting factors can be updated based on the current patient data continuously, periodically, at a predetermined time, etc. —e.g., the weighting factor(s) can be updated based on when the current patient data is received. In some embodiments, a weighting factor is assigned to each disturbance profile—e.g., if disturbance profile-1 has a very poor match with current patient data then it may be assigned a weighting factor of 0.0 or near 0.0, if disturbance profile-2 has a moderate match with current patient data then it may be assigned a weighting factor of 0.5, if disturbance profile has a very good match with current patient data then it may be assigned a weighting factor of 1.0 or near 1.0. A cost function, objective function, lost function, etc. can then be applied to all weight-factored disturbance profiles (or any number or combination of weight-factored disturbance profiles) to determine the best (e.g., via optimization) insulin dose amount.

Other data processing can be performed on any one or combination of disturbance profiles, such as smoothing, weighting, etc. For instance, any one or combination of disturbance profiles can be smoothed and applied to a weighting function so as to emphasize or deemphasize certain disturbance profiles. It may be, for example, desired to deemphasize a portion of a disturbance profile that pertain to times when the patient is sleeping (e.g., from 10:00 PM to 6:00 AM). This may be done to cause the disturbance profile probability to return its prior value every 6:00 AM.

There may be instances where the current patient data does not match with any disturbance profile. In this situation, the processor 1102 can create, or at least begin to create, a new disturbance profile. The new disturbance profile can be stored in memory along with the plural disturbance profiles. In addition, or in the alternative, the processor 1102 can update or modify an existing disturbance profile.

Any one or combination of disturbance profiles and/or the predictive model can be stored in the memory associated with the processor 1102. Alternatively, any one or combination of the disturbance profiles and/or the predictive model can stored in a memory external to the processor 1102, wherein the processor 1102 can be configured to be in communication with the external memory.

The processor 1102 can be configured by the instructions 1124 to output a signal representative of the insulin dose amount to a device 1004 configured for monitoring, influencing, and/or administering insulin levels in the patient. In addition, or in the alternative, the instructions 1124 can cause the processor 1102 to factor in additional data, such as certain attributes of the current patient data, previous insulin dose amount data, total daily insulin (TDI) data, insulin on board (JOB) data, etc., and use this/these data to modify the determined insulin dose amount. The processor 1102 can be configured by the instructions 1124 to output a signal representative of the modified insulin dose amount to the device 1004. The instructions 1124 can cause the processor 1102 to output a modified insulin dose amount signal in lieu of the insulin dose amount, output the modified insulin does amount and the insulin dose amount, output the insulin does amount with an indicator that the modified insulin does amount is recommended, etc.

The current patient data may indicate that the patient has entered into or has a high risk of entering hyperglycemia or hypoglycemia. Thus, the processor 1102 can be configured by the instructions 1124 to determine if there is any current deviation from a threshold blood glucose level that increases a risk of hyperglycemia and/or hypoglycemia. Using this current deviation assessment, the processor 1102 can be configured by the instructions 1124 to determine an insulin dose amount to be administered based on the current deviation as opposed to being based on the anticipated disturbance profile(s). In the alternative, the processor 1102 can be configured by the instructions 1124 to modify the insulin dose amount that is based on the anticipated disturbance profile to account for the current deviation. The instructions 1124 can cause the processor 1102 to output this modified insulin dose amount signal in lieu of the insulin dose amount, output this modified insulin does amount and the insulin dose amount, output the insulin does amount with an indicator that this modified insulin does amount is recommended, etc.

The historical patient data and the current patient data can be generated by a device 1004. This device 1004 can be in communication with the processor 1102 and/or the memory with which the processor 1102 is in communication or to which is otherwise accessible—e.g., the device 1004 can transmit the patient data directly to the processor 1102, the device 1004 can transmit the patient data to the memory from which the processor 1102 receives the data, or a combination thereof. The device 1004 can measure/obtain/collect/generate the patient data continuously, periodically, at a predetermined time, as demanded by a user of the device 1004, as demanded by a user of the processor 1102, as prescribed by an algorithm of the device 1004, as prescribed by an algorithm of the processor 1102, etc. The data transmission from the device 1004 or memory to the memory or processor 1102 can be a push operation, a pull operation, or a combination thereof. The device 1004 can be a glucose monitoring device, an activity tracking device, a meal tracking device, etc., any one of which having a processor configured to perform functions of measuring/obtaining/collecting/generating patient data. Any one or combination of these devices 1004 can be in communication with the processor 1102 or the memory associated with or in communication with the processor 1102. Thus, the processor 1102 can be configured to receive the historical patient data and/or the current patient data from the glucose monitoring device, the activity tracking device, and/or the meal tracking device. Alternatively, the glucose monitoring device, the activity tracking device, and/or the meal tracking device can be configured to transmit the historical patient data and/or the current patient data to a data store 1002, wherein the processor 1102 is configured to receive the historical patient data and/or the current patient data from the data store 1002.

The output of the processor 1102 can be configured for display 1110 on a display screen (e.g., via a user interface), as a command signal to control an insulin device, as a communication signal to generate an alert or notification, as an input for a monitoring device, etc. Thus, the output can be configured for transmitting to a device 1004 comprising any one or combination of an insulin delivery device, a glycemic state monitoring device, a glucose management system, an insulin recommendation system, etc. In addition, or in the alternative, the output can be transmitted to a memory with which any of these devices 1004 are in communication. The transmission from the processor 1102 or memory to the memory or device 1004 can be continuously, periodically, at a predetermined time, as demanded by a user of the device 1004, as demanded by a user of the processor 1102, as prescribed by an algorithm of the device 1004, as prescribed by an algorithm of the processor 1102, etc. The data transmission to the device 1004 or memory from the memory or processor 1102 can be a push operation, a pull operation, or a combination thereof. Any one or combination of these devices can include a processor configured for performing the functions of dose delivery, monitoring, displaying, managing, etc. Any of these devices 1004 can be part of or configured to operate within an open loop system, closed loop system, bolus priming system, artificial pancreas system, etc. For instance, the processor 1102 can be a control module of an automated insulin dosing system.

Thus, the instructions 1124 can cause the processor 1102 to: 1) configure the output signal as a notification communication causing the device 1004 to recommend administration of the insulin dose amount and/or modified insulin dose amount; 2) configure the output signal as a command signal causing the device 1004 to administer the insulin dose amount and/or modified insulin dose amount; and/or 3) configure the output signal as a data point to allow the device 1004 to graphically display the insulin dose amount and/or modified insulin dose amount.

An exemplary embodiment relates to a computer readable medium 1122 having instructions 1124 stored thereon that when executed by a processor causes 1102 the processor to execute an algorithm. The instructions 1124 can cause the processor 1102 to generate plural disturbance profiles, each disturbance profile being a data representation based on historical patient data pertaining to a deviation from a threshold blood glucose level. The instructions 1124 can cause the processor 1102 receive current patient data. The current patient data and/or the historical patient data can include any data indicative of a patient characteristic. The instructions 1124 can cause the processor 1102 apply a predictive model. The instructions 1124 can cause the processor 1102 to compare the current patient data to at least one disturbance profile. The instructions 1124 can cause the processor 1102 to assess the likelihood of a disturbance profile of the plural disturbance profiles being an anticipated disturbance profile via probability analysis. The anticipated disturbance profile can be a disturbance profile that is determined to match with the current patient data based on the probability analysis. The instructions 1124 can cause the processor 1102 to determine an insulin dose amount based on the anticipated disturbance profile. The instructions 1124 can cause the processor 1102 to output a signal representative of the insulin dose amount to a device 1004 configured for monitoring, influencing, and/or administering insulin levels in the patient.

An exemplary embodiment relates to a method for informing, determining, or controlling insulin dosage. The method can involve generating plural disturbance profiles, each disturbance profile being a data representation based on historical patient data pertaining to a deviation from a threshold blood glucose level. The method can involve receiving current patient data. The current patient data and/or the historical patient data can include any data indicative of a patient characteristic. The method can involve applying a predictive model. The current patient data can be compared to at least one disturbance profile. The probability analysis can be used to assess the likelihood of a disturbance profile of the plural disturbance profiles being an anticipated disturbance profile, the anticipated disturbance profile being a disturbance profile that is determined to match with the current patient data based on the probability analysis. The method can involve determining an insulin dose amount based on the anticipated disturbance profile. The method can involve outputting a signal representative of the insulin dose amount to a device configured for monitoring, influencing, and/or administering insulin levels in the patient.

EXAMPLES

The discussion below relates to exemplary implementations and test results pertaining to embodiments of the disclosure. It is understood that the following examples are non-limiting examples of how to make, use, and test the systems, apparatuses, and methods disclosed herein.

Example 1

Hyperglycemia following meals is a recurring challenge for people with type 1 diabetes, and even the most advanced available automated systems currently require manual input of carbohydrate amounts. To progress towards fully automated systems, the exemplary implementation provides a control system that can automatically deliver insulin dosage amounts or recommendations, priming boluses, anticipate eating behaviors, anticipated physical activity behaviors, etc. to improve postprandial closed-loop or opened-loop control.

A model predictive control (MPC) system was enhanced by an automated bolus system reacting to early glucose rise and/or a multistage MPC (MS-MPC) framework to anticipate historical patterns. Priming was achieved by detecting large glycemic disturbances, such as meals, and delivering a fraction of the patient's TDI modulated by the disturbance's likelihood (bolus priming system, BPS). In the anticipatory module, glycemic disturbance profiles were generated from historical data using clustering to group days with similar behaviors; the probability of each cluster is then evaluated at every controller step and informs the MS-MPC framework to anticipate each profile. Four configurations were tested: MPC, MPC+BPS, MS-MPC, and MS-MPC+BPS in simulation to contrast the effect of each controller module.

As will be explained in more detail, results show that postprandial time in range was highest for MS-MPC+BPS: 60.73±25.39%, but improved with each module: MPC+BPS: 56.95±25.83 and MS-MPC: 54.83±26.00%, compared to MPC: 51.79±26.12%. Exposure to hypoglycemia was maintained for all controllers (time below 70 mg/dL<0.5%), and improvement came primarily from a reduction in postprandial time above range (MS-MPC+BPS: 39.10±25.32%, MPC+BPS: 42.99±25.81%, MS-MPC 45.09±25.96%, MPC 48.18±26.09%). The bolus priming system and anticipatory disturbance profiles improved BG control and were most efficient when combined.

Fully Closed-Loop AID

Several AID systems that do not require users to input meal amounts have been tested. In 2014, Harvey et al. evaluated a fully closed loop (FCL) AID system on 12 adult participants with T1D in an inpatient clinical tria. Overall, this system produced glycemic control with 80% of all BG readings in the 70-180 mg/dL range (time in range, TIR) but caused high postprandial glucose values following unannounced meals. Forlenza et al. presented the performance of an FCL that preempts predefined postprandial excursions in a 72-hour hotel-based study, reporting a TIR of 63.6±9.2%. However, in the four hours following unannounced meals, the time above range (>180 mg/dL, TAR) was 60.9±23.3%. A recent study by Dovc et al. used two formulations of insulin, FIASP and Aspart, in a 27-hour inpatient admission study of their FCL AID system, reporting TIR of 53.3% and 57.9% for Aspart and FIASP insulins, respectively. Their approach relied on a meal detection algorithm but similarly faced difficulty with unannounced meals. Multi-hormone approaches have reported better performances, with recent early outpatient results. In 2021, Haidar et al. conducted a 30 participant open-label crossover trial and showed that an AID system using simple meal announcements and empagliflozin was non-inferior to a hybrid system with meal announcements (mean BG: 153±25.2 vs. 153±27.0 mg/dL). Majdpour et al. demonstrated the non-inferiority of an insulin-pramlintide FCL AID to a hybrid AID (TIR: 81% vs. 83%) in another 2021 pilot study.

Cameron's 2012 manuscript describes a methodology for an automated insulin dosing system that uses multiple BG prediction models, each informed by different disturbances. When the system determines that one disturbance is more likely, additional weight is given to that model's predictions. Additionally, information was included regarding the likely timing of meal disturbances based on normal mealtimes, the time of the last meal, and sleep schedule. Using this approach, Cameron et al. were able to reduce the two-hour prediction error by 45% without meal detection and 18% with meal detection. The three-hour prediction error was reduced by 60% without meal detection and 30% with it.

Cameron et al. extended these findings in a 2014 clinical trial. The so-called multiple model probabilistic controller (MMPC) was used by ten patients in an inpatient study where they consumed five unannounced meals. For the six patients who used the final version of the controller, the mean continuous glucose monitoring (CGM) TIR was 78%. During the admission, there was only one controller-induced hypoglycemia.

The MMPC was evaluated on ten patients in an inpatient clinical study where the mean TIR was 142 mg/dL overall and 125 mg/dL overnight. A different version of the algorithm that was tested in a hotel-based study with 15 subjects achieved an overall mean BG of 152 mg/dL and a mean overnight BG of 139 mg/dL.

Use of Behavioral Patterns to Anticipate Glycemic Disturbances

Several simulation and clinical experiments have shown how anticipatory profiles integrated into AID systems can reduce the unwanted effects of glycemic disturbances. Simulation experiments have demonstrated that multistage model predictive (MS-MPC) controllers informed by disturbance profiles to anticipate moderate exercise's effects can reduce hypoglycemia, results that were later confirmed in a randomized crossover clinical trial with 15 adult participant: there were fewer hypoglycemic events (9 vs. 33), and the percent time where BG was <70 mg/dL (time below range, TBR) was 1.3% lower while the participants used the MS-MPC system compared to a well-tuned standard MPC. The overall reduction in hypoglycemia resulted in no significant increase in TAR.

In-silico experiments also demonstrated the capacity of the MS-MPC framework to anticipate glycemic disturbances caused by meals. In that work, disturbance profiles were generated from a representative real subject and then used to perform closed-loop experiments using the 100 adult cohort of the University of Virginia (UVA)/Padova simulator. Results showed an average increase in TIR of 1.6% when using a hybrid closed-loop approach and 16.4% when using an FCL approach.

One of the goals in this experiment is to build upon past experiences and further study the impact of automated priming bolus and disturbance anticipation using the MS-MPC framework. To test the effects of each component of the control system, a 2×2 experimental design (each module on or off) was implemented, resulting in four treatment strategies: model MPC, MS-MPC, MPC+BPS, and MS-MPC+BPS.

12

Methods
Control Strategy

Figure 2:
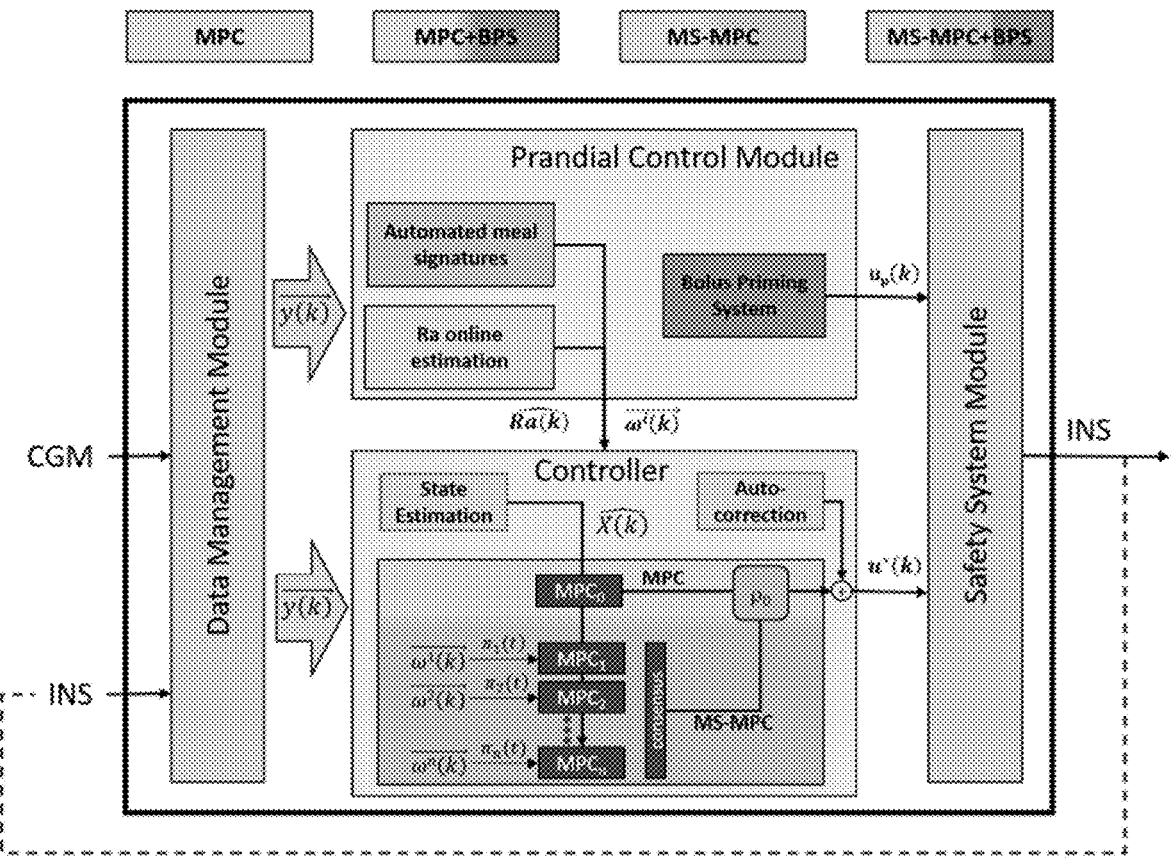
FIG. 2 shows an exemplary schematic of control strategies tested.

An exemplary modular control strategy is depicted in FIG. 2. Using legacy modular architecture (e.g., data management, safety system module, auto-correction, state estimation) as a guide, four different combinations of modules to reject large positive disturbances are considered.

Core Controller

Rather than a single control strategy, MPC encompasses a general control paradigm; it integrates the predictions from an explicit mathematical model of the user's glucose-related metabolic state within a real-time optimization problem that aims to find the best insulin injection subject to possible constraints over the model variables. In this setup, the MPC part commands optimized basal insulin injections through the pump every five minutes to reject internal metabolic disturbances. MS-MPC is a robust control strategy that considers N parallel MPC controllers, each perturbed by a particular disturbance realization. In this case, the disturbance realizations are composed of N different subject-specific disturbance profiles representing typical eating behavior. The final control action is reached after a consensus of the N controllers by the non-anticipatory constraint.

Subject Specific Disturbance Profile Generation

To construct a manageable ensemble of disturbance profiles for the MS-MPC to anticipate, the current ensemble of d (t) signatures was reduced to a few representative profiles. To do so, the occurrence of noticeable disturbances are clustered, and then a representative disturbance input for each cluster is constructed. This necessitates (i) the construction of disturbance signatures, (ii) detection of disturbance events, (iii) clustering daily patterns of detected events, and (iv) the construction of signatures that represent each cluster. This process is detailed below.

Historical Disturbance Estimation

Figure 3:
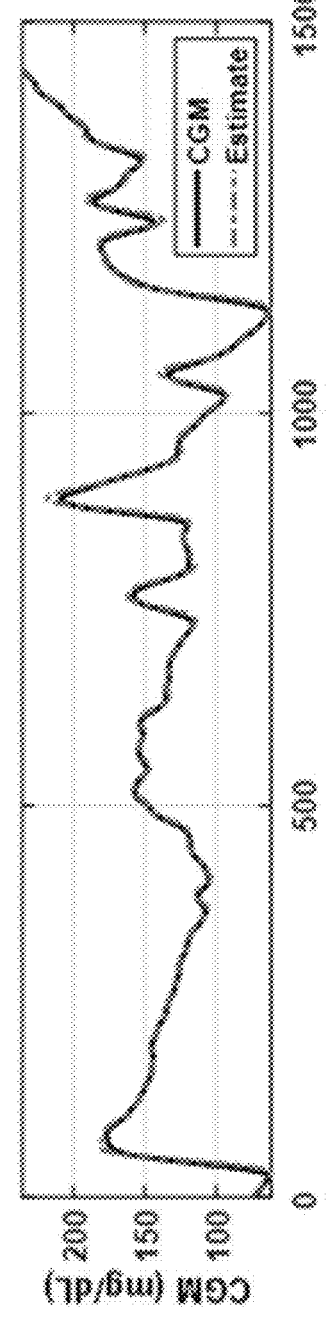
FIG. 3 shows CGM data of one subject.
Figure 4:
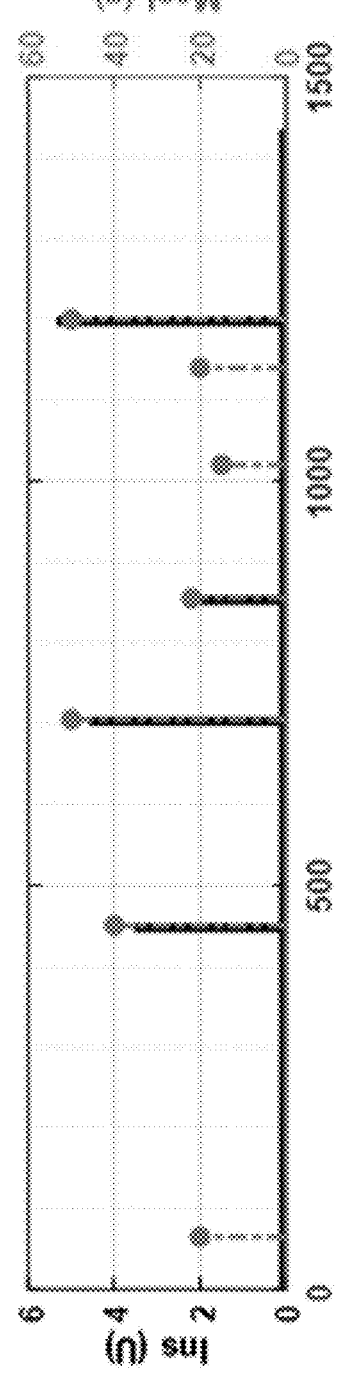
FIG. 4 shows insulin data of one subject.
Figure 5:
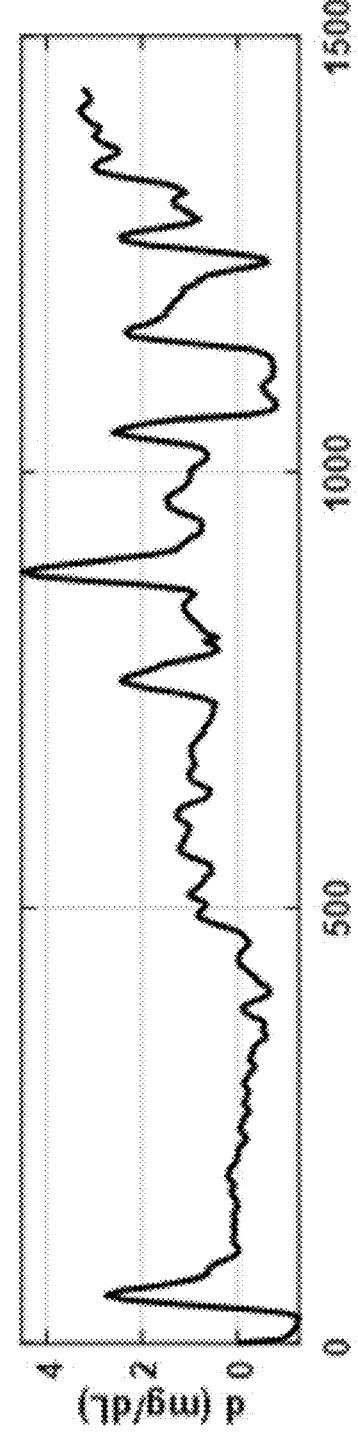
FIG. 5 shows an estimation of disturbance signature, d.

Disturbance signatures, d (t), are estimated for each day of the historical record using a Kalman Filter (KF) with the same internal model as the controller (e.g., based on CGM and insulin only, not the meal record). In this case, the operating point for the linearization of the model is defined based on that subject's mean CGM value for the day, the basal rate, and the steady-state solution of the model equations. KF tuning was performed by modifying the covariance matrices for measurement (R) and modeling (Q) noises. Variations on R and the diagonal elements of Q matrix in the range [$1\times10^{-4}$ $1\times10^{4}$] were tested to determine values that, in addition to a smoother estimation of the d (t) signature, adequately represented a system input to reflect the meal-related fluctuations in glucose observed in the CGM. Thus, values for Q and R were fixed in such a way that d had suitable behavior representing food intake during high glucose excursions. FIG. 3 shows CGM data of one subject; FIG. 4 shows insulin data of one subject; and FIG. 5 shows an estimation of disturbance signature, d.

Kalman Filter Design

KF is designed from a linearized version of the controller model given by the following equations:

$$\dot{G} = -S_g(G - G_b) - S_I X \cdot G + d(t),\tag{1}$$

$$\dot{X} = -p_2 X + p_2(I - I_b),\tag{2}$$

$$\dot{I}_{sc1} = -(k_1 + k_d)I_{sc1} + J(t),\tag{3}$$

$$\dot{I}_{sc2} = -k_2 I_{sc2} + k_d I_{sc1},\tag{4}$$

-continued $$\dot{I} = -nI + \frac{IR_a}{V_I \cdot BW}, \tag{5}$$

Model parameters were identified from data collection for each subject, and the operating point was based on the mean value of CGM per day, the subject-specific basal rate, and the steady-state solution of the model equations. After linearization, by discretizing and incorporating uncertainty in the dynamics of the discretized system ($w_k$) and the noise in the discrete-time measurements ($v_k$), the model can be written as:

$$x_{k+1}=f(x_k,u_k,d_k)+w_k, \tag{6}$$

$$y_k=g(x_k)+v_k, \tag{7}$$

$f(\bullet)$ and $g(\bullet)$ are linear functions, and $x_k=[G, X, I_{sc1}, I_{sc2}, I]^T$, $u_k=J$, and $y_k=G$ the state, input and output vectors, respectively. A normal distribution with median zero and covariance matrixes Q and R are assumed for $w_k$ and $v_k$, respectively. Then, the KF is design according to $$\hat{x}_{k+1}=f(\hat{x}_k,u_k,\hat{d}_k)+K_k(y_k-\hat{y}_k), \tag{8}$$

$$\hat{y}_k=g(\hat{x}_k), \tag{9}$$

with $(y_k-\hat{y}_k)$ the observer error and $K_k$ the observer gain computed by solving the Riccati equation as a function of Q and R.

Disturbance Detection

As records of meals would be absent in a full-closed loop system, meal-like disturbances were reconstructed retrospectively from CGM and insulin data. To filter out any small deviation and focus on disturbances worth anticipating, an automated disturbance detector using features characterizing the estimated disturbance values, d, and continuous glucose measurements, cgm, for each day of historical data collected were used. These features were selected to represent the changes in the glucose and disturbance values characteristic of glycemic disturbances, such as meals. Descriptions of the features which were calculated for each five-minute sample are listed in Table 1.

TABLE 1

| Features for the retrospective disturbance detection algorithm | |
|---|---|
| Feature | Description |
| $f_1$ | Intercept term from $2^{nd}$ order polynomial fit on $c_1$ = cgm(t − 6), . . . , cgm(t + 6) |
| $f_2$ | Slope term from $1^{st}$ order polynomial fit on $c_2$ = cgm(t), . . . , cgm(t + 12) |
| $f_3$ | Curvature term from $2^{nd}$ order polynomial fit on $c_1$ = cgm(t − 6), . . . , cgm(t + 6) |
| $f_4$ | $f_2 \cdot f_3$ |
| $f_5$ | Intercept term from $2^{nd}$ order polynomial fit on $d_1$ = d(t − 6), . . . , d(t + 6) |
| $f_6$ | Slope term from $1^{st}$ order polynomial fit on $d_2$ = d(t), . . . , d(t + 6) |
| $f_7$ | Curvature term from $2^{nd}$ order polynomial fit on $d_1$ = d(t − 6), . . . , d(t + 6) |
| $f_8$ | $f_6 \cdot f_7$ |
| $f_9$ | Maximum d value in the next hour $d_{max}$ = max $d_2$ |

After features were generated for each five-minute interval, t, the probability of a large disturbance, $\pi_{detect}(t)$, is determined using logistic regression (see Table 2). The detection times are determined by finding the local minimums of CGM values when the detection vector was equal to one at least 60 minutes apart (or the first index if there were no local minimums). If detection times were within one hour of each other, the first detection time was used.

TABLE 1

| Logistic regression parameter values | | |
|---|---|---|
| Variable | Description | Value |
| $\beta_0$ | Intercept for the logistic regression equation | −1.1584 |
| $\beta_1$ | Logistic regression coefficient term for $f_1$ | 14.6012 |
| $\beta_2$ | Logistic regression coefficient term for $f_2$ | 0.0135 |
| $\beta_3$ | Logistic regression coefficient term for $f_3$ | −0.0111 |
| $\beta_4$ | Logistic regression coefficient term for $f_4$ | −0.4954 |
| $\beta_5$ | Logistic regression coefficient term for $f_5$ | 2661.6419 |
| $\beta_6$ | Logistic regression coefficient term for $f_6$ | −0.2154 |
| $\beta_7$ | Logistic regression coefficient term for $f_7$ | −2.4333 |
| $\beta_8$ | Logistic regression coefficient term for $f_8$ | −13551.6432 |
| $\beta_9$ | Logistic regression coefficient term for $f_9$ | 2.9627 |
| $\tau_{threshold}$ | Probability detection threshold | 0.3590 |

Disturbance Profiles Generation

Figure 6:
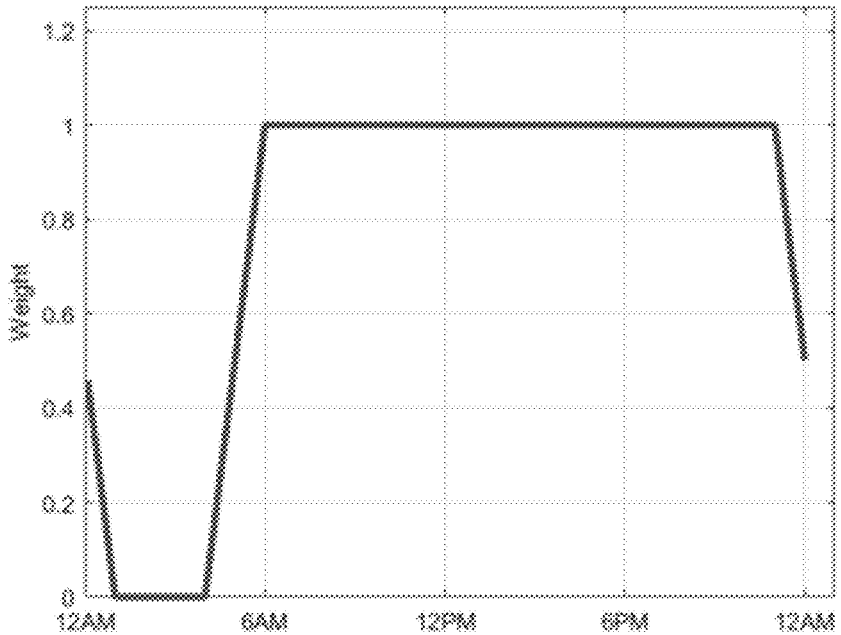
FIG. 6 illustrates the effect of a weighting function applied to profile values.

After major glycemic disturbances are detected, daily indicator signals are defined to group similar days into clusters (equal to one in the two hours following disturbance detections and zero otherwise). Using k-means with the hamming distance measure, these signals are clustered with k=1, . . . , 5. The number of clusters, k, for each individual is based on which produced the highest Calinski-Harabasz score, maximizing cluster separation and cohesion. After days of data were grouped, the profile trace, co, for each cluster, i, at each five-minute interval of the day, j, is determined from the average of each day in the cluster's disturbance signal in that five-minute interval, $d_{m,j}$.

$$\omega_{i,j} = \frac{1}{n_{days,i}} \cdot \sum_{m=1}^{n_{days,i}} d_{m,j} \text{ for } i = 1, \dots, n_{clusters} \text{ and } j = 1, \dots, 288 \tag{10}$$

with $n_{days,i}$ as the number of days grouped into cluster i. These profiles are then smoothed using a centered moving average over an hour. The values are multiplied by a weighting function shown in FIG. 6 to deemphasize profiles overnight, allowing for the profile probabilities to return to their prior value at the beginning of each day.

The prior probability value for each cluster, $\pi_{prior,i}$, is estimated as the proportion of days of data that were assigned to that given cluster.

$$\pi_{prior,i} = \frac{n_{days,i}}{n_{days,total}} \tag{11}$$

where $n_{days,i}$ was the number of days of data in cluster i and $n_{days,total}$ represented the total number of days considered. These prior probability values serve as a starting point so that the initial weight of each profile in the MS-MPC is related to historical data.

Disturbance Profiles Generation

Figure 7:
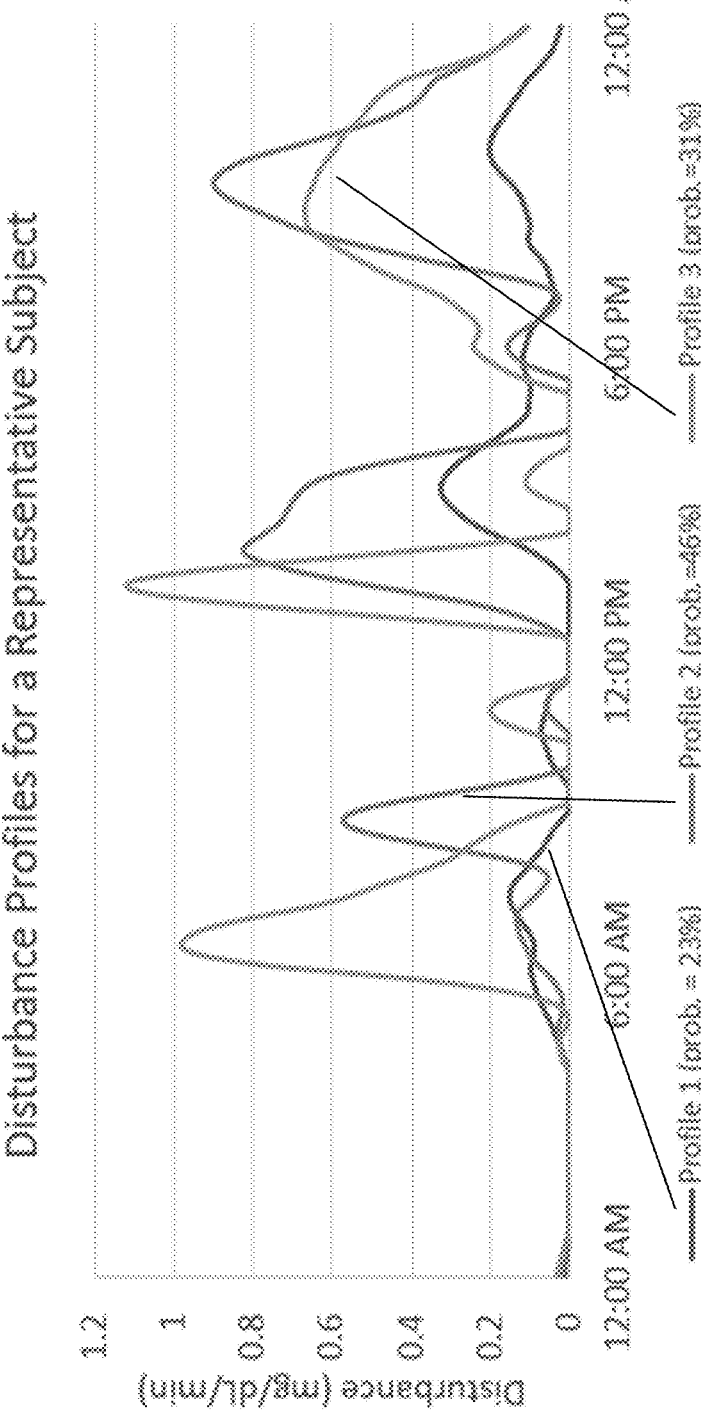
FIG. 7 shows disturbance profiles for a representative subject.

FIG. 7 shows an example of one subject's profiles. Here it can be seen that this individual's disturbance profiles are elevated following typical times for breakfast (6:00-8:00 AM), lunch (12:00-2:00 PM), and dinner (6:00-8:00 PM). The associated prior probabilities indicate that this person eats earlier on 31% of days, and on 46% of the days of data used, the subject ate later. On 23% days, they had less of a discernable pattern of eating determined from their detected disturbances.

Profile Probability Estimation for Online MS-MPC Weighing

The probability value of each profile is updated in real-time based on the current disturbance measurement, which was found using the same technique applied to the retrospective data. This probability, $\pi_i(t)$, is estimated using the method developed by Patek et al. This process allows each profile's probabilities to be shifted dynamically following the disturbance currently being experienced by the user.

A "night mode" is further added, allowing the profile probabilities real-time estimates to reset back to their prior (so each day is not influenced by the previous one). From 11:00 PM to 1:00 AM, the probabilities devolved linearly from the value before the beginning of night mode, $\pi_{i,night}$, to the prior, $$l_{d,i}(n) = \frac{\pi_{prior,i} - \pi_{i,night}}{24} \cdot n + \pi_{i,night} \text{ for } n = 1, \ldots, 24. \quad (12)$$

For the, n, intervals after the beginning of night mode, $$\pi_i(t) = l_{d,i}(n). \quad (13)$$

To ensure that the currently observed disturbance is prioritized over anticipation of expected disturbances, all the profile probability values are scaled based on an index, $\rho_0$, derived from the level of the current disturbance estimate, $\hat{d}(t)$. The calculation for $\rho_0$ is detailed in the below.

Calculation of Probability of Current Disturbance Estimate $$\gamma_1 = \frac{\ln 81}{dh_{max} - dh_{min}}, \gamma_2 = \frac{\ln 81}{\pi_{max} - \pi_{min}}, \quad (14)$$

$$a_1 = \frac{1}{8}\left(e^{-\gamma_1 \cdot dh_{min}} - 9e^{-\gamma_1 \cdot dh_{max}}\right), \quad (15)$$

$$a_2 = \frac{1}{8}(e^{-\gamma_2 \cdot \pi_{min}} - 9e^{-\gamma_2 \cdot \pi_{max}}), \quad (16)$$

$$\rho_0 = \min\left(\frac{a_1}{a_1 + e^{-\gamma_1 \cdot \hat{d}(t)}} + \frac{a_2}{a_2 + e^{-\gamma_2 \cdot \pi_{disturbance}(t)}}, 0.99\right), \quad (17)$$

where $$[dh_{min}, dh_{max}] \subset [0, 10], [\pi_{min}, \pi_{max}] \subset [0, 10], \quad (18)$$

$$\gamma_1 = \frac{\log(81)}{dh_{max} - dh_{min}}, \gamma_2 = \frac{\log(81)}{\pi_{max} - \pi_{min}}, \quad (19)$$

The final adjusted probabilities, $\pi_{adjusted,i}(t)$, were found by multiplying the profile probabilities by $1-\rho_0$.

$$\pi_{adjusted,i}(t) = \pi_i(t) \cdot (1-\rho_0) \quad (10)$$

Experimental Design

Data collected during the unsupervised at-home portion of a large-scale pivotal trial conducted at UVA (NCT03563313) was used to evaluate an embodiment of the method. This data is from 124 adult and adolescent participants with T1D over six months, during which they used an automated insulin delivery (AID) system with meal announcements. 100 clinical subjects' data were randomly selected and paired to an in-silico subject in the UVA/Padova T1D simulator platform. 80% of the data was used to create meal profile clusters. Seven days with at least one recorded meal were randomly selected from the remaining month of collected data. This week of meal record, scaled by the bodyweight, was then used as the meal protocol of the simulation experiment, which included intraday insulin sensitivity variability. In this implementation of the simulation platform, circadian changes to insulin sensitivity and dawn phenomenon are simulated using subject-specific (e.g., class-specific) time-varying profiles, which impacts endogenous glucose production and insulin-dependent glucose utilization. The use of real eating records allowed for more realistic behaviors in simulation and the existence of eventual meal patterns. This experimental configuration was then tested with the four configurations of the control system: MPC, MS-MPC, MPC+BPS, MS-MPC+BPS. Treatments were compared overall and during the four hours after meals using the relevant metrics described by Maahs et al.'s criteria for evaluating AID systems. Statistical significance was not reported because the assumptions of such tests are not particularly informative in a simulation environment.

Results

The simulation experiment results suggest that the use of the anticipatory profiles in the MS-MPC and the BPS reduced BG values overall. The primary outcome (TIR over the entire simulation) improved from 72±17.7% with MPC only to 73.4±17.4% with anticipation and 75.5±17.1% with priming bolus. Maximum effect was seen with the combination of priming bolus and anticipation with TIR reaching 77.2±16.7%, or +5.2% over MPC alone. On average, when delivered BPS boluses were 27.64±29.70 minutes after the actual mealtime. 4% of the patients' TDI was delivered after 64.11% of meals, 7% was delivered after 36.72%, and 10% was delivered after 22.18%. No BPS dose was delivered after 35.89% of meals. The overall false positive rate was 0.69%.

The mean BG for the MS-MPC+BPS was the lowest (155.14±31.88 mg/dL). The other controller configurations had higher mean BG values of 165.49±33.49, 161.61±33.60, and 159.65±33.20 mg/dL for the MPC, MS-MPC, and MPC+BPS, respectively. This trend in lower BG values was represented similarly in the time below ranges (e.g., <50, <60, and <70 mg/dL), time in tight range (e.g., 70-140 mg/dL), and time above ranges (e.g., >180, >250, and >300 mg/dL). The BPS and anticipatory profiles also reduced the standard deviation of BG values and caused the system to deliver more insulin overall. The overall results of the experiment are listed in Table 3.

TABLE 3

| Artificial pancreas evaluation metric mean and standard deviation values from simulation experiments overall | | | | |
| --- | --- | --- | --- | --- |
| Controller | MPC | MS-MPC | MPC + BPS | MS-MPC + BPS |
| <50 mg/dL (%) | 0.03 ± 0.21 | 0.07 ± 0.40 | 0.02 ± 0.15 | 0.14 ± 0.54 |
| <60 mg/dL (%) | 0.06 ± 0.41 | 0.23 ± 0.85 | 0.10 ± 0.45 | 0.33 ± 1.01 |
| <70 mg/dL (%) | 0.14 ± 0.64 | 0.47 ± 1.37 | 0.24 ± 0.81 | 0.65 ± 1.58 |
| 70-140 mg/dL (%) | 49.16 ± 17.94 | 50.35 ± 19.25 | 51.92 ± 17.61 | 53.81 ± 18.89 |
| 70-180 mg/dL (%) | 72.02 ± 17.67 | 73.37 ± 17.38 | 75.50 ± 17.07 | 77.17 ± 16.73 |

TABLE 3-continued

| Artificial pancreas evaluation metric mean and standard deviation values from simulation experiments overall | | | | |
|---|---|---|---|---|
| Controller | MPC | MS-MPC | MPC + BPS | MS-MPC + BPS |
| >180 mg/dL (%) | 27.85 ± 17.47 | 26.16 ± 17.25 | 24.27 ± 16.84 | 22.18 ± 16.45 |
| >250 mg/dL (%) | 9.92 ± 11.51 | 9.31 ± 11.25 | 7.66 ± 10.71 | 7.02 ± 10.28 |
| >300 mg/dL (%) | 4.81 ± 8.29 | 4.52 ± 8.03 | 3.74 ± 7.86 | 3.43 ± 7.36 |
| Mean (mg/dL) | 165.49 ± 33.49 | 161.61 ± 33.60 | 159.65 ± 33.20 | 155.14 ± 31.88 |
| Standard Deviation (mg/dL) | 53.90 ± 33.49 | 53.62 ± 32.72 | 49.51 ± 34.32 | 48.91 ± 32.82 |
| CV (%) | 30.46 ± 12.09 | 31.12 ± 11.89 | 28.85 ± 12.01 | 29.44 ± 11.88 |
| Total Daily insulin (u) | 36.72 ± 17.33 | 37.65 ± 17.57 | 38.09 ± 18.04 | 39.20 ± 18.34 |

In the four hours following meals, the effect of the anticipatory profiles and BPS was more evident. During this period, the TIR was 60.73±25.39% for the MS-MPC+BPS. The mean TIR was 3.78%, 5.9%, and 8.94% less for the MPC+BPS, MS-MPC, and MPC configurations respectively. Postprandial mean BG was also 4.51-10.35 mg/dL lower for the MS-MPC+BPS than it was for the other controller setups. TBR for all controller setups was less than 1% during this timeframe. Table 4 lists the results during the postprandial period.

The most insulin was used in the case where both the BPS and profiles were active (MS–MPC+BPS). This was less when only BPS was used (MPC+BPS), then even less when just the profiles were used (MS-MPC), and the least when the standard MPC. Interestingly, the MS-MPC case had the highest average CV, followed by MPC, MS-MPC+BPS, and MPC+BPS.

The postprandial TIR was increased by nearly 10% when the anticipatory profiles and BPS were used compared to the standard MPC. Additionally, there was an increase in the

TABLE 4

| Artificial pancreas evaluation metric mean and standard deviation values from simulation experiments during the four hours after meals | | | | |
|---|---|---|---|---|
| Controller | MPC | MS-MPC | MPC + BPS | MS-MPC + BPS |
| <50 mg/dL (%) | 0.00 ± 0.02 | 0.00 ± 0.02 | 0.00 ± 0.01 | 0.03 ± 0.15 |
| <60 mg/dL (%) | 0.01 ± 0.08 | 0.03 ± 0.16 | 0.01 ± 0.06 | 0.08 ± 0.33 |
| <70 mg/dL (%) | 0.03 ± 0.17 | 0.08 ± 0.33 | 0.06 ± 0.32 | 0.17 ± 0.53 |
| 70-140 mg/dL (%) | 23.02 ± 18.78 | 27.79 ± 22.09 | 25.67 ± 18.92 | 31.24 ± 22.28 |
| 70-180 mg/dL (%) | 51.79 ± 26.12 | 54.83 ± 26.00 | 56.95 ± 25.83 | 60.73 ± 25.39 |
| >180 mg/dL (%) | 48.18 ± 26.09 | 45.09 ± 25.96 | 42.99 ± 25.81 | 39.10 ± 25.32 |
| >250 mg/dL (%) | 17.87 ± 19.85 | 16.61 ± 19.28 | 13.77 ± 18.46 | 12.46 ± 17.91 |
| >300 mg/dL (%) | 8.68 ± 14.73 | 8.13 ± 14.34 | 6.69 ± 13.77 | 6.19 ± 13.16 |
| Mean (mg/dL) | 197.20 ± 54.44 | 191.11 ± 54.17 | 188.59 ± 54.36 | 181.72 ± 52.27 |
| Standard Deviation (mg/dL) | 53.87 ± 30.73 | 54.59 ± 30.37 | 49.67 ± 32.03 | 50.00 ± 30.96 |
| CV (%) | 25.69 ± 9.09 | 26.97 ± 8.95 | 24.61 ± 8.96 | 25.83 ± 8.76 |
| Insulin Delivered (u) | 3.52 ± 1.92 | 3.61 ± 1.98 | 3.67 ± 2.07 | 3.79 ± 2.13 |

Discussion

This simulation, which encompasses realistic eating behaviors in T1DM, indicates that mean BG values were lowest for the MS-MPC+BPS, followed in order by the MPC+BPS, the MS-MPC, and the MPC both overall and after eating. This relationship was maintained in terms of the percent time where BG was in the euglycemic ranges (e.g., 70-140 mg/dL and 70-180 mg/dL) and the hypoglycemic ranges (e.g., <50, <60, and <70 mg/dL). It was reversed in the amount of time where BG was in the hyperglycemic ranges (e.g., >180, >250, and >300 mg/dL). This shows that both the anticipatory profiles and the BPS had the effect of lowering BG values overall. Overall, the MPC+BPS had a 5.84 mg/dL lower mean BG and TIR 3.38% higher than the MPC. The MS-MPC case resulted in a 1.35% greater TIR compared to the MPC, where no profiles were used. The MPC+BPS and MS-MPC+BPS cases had a difference of 1.67% in TIR. This indicates a synergetic interaction between BPS and the anticipatory disturbance profiles.

Across the four configurations, there was no meaningful change in the amount of hypoglycemia overall. Comparing the MPC and MS-MPC+BPS shows that the modules may be responsible for increasing the amount of TBR by less than five minutes while increasing TIR by more than 5% overall, which is clinically relevant.

70-140 mg/dL range, but this amount was slightly smaller. This difference resulted from a reduction in TAR and a reduction in the mean BG of roughly 16 mg/dL. The combination of the MS-MPC structure and BPS had its greatest effect during the postprandial period by lowering BG values without increasing hypoglycemia.

Conclusion

This experiment shows that in a simulation environment, both the BPS and the disturbance profiles positively impact the amount of time that BG values are in the euglycemic range while also decreasing hyperglycemia. These modules are the most impactful during the four hours following eating. Independently both modules improve TIR and do even better in combination. The reduction in mean BG values attributed to the BPS and disturbances profiles did increase hypoglycemia, but only to a degree that is not clinically meaningful. The BPS and disturbance profiles seem to impact the variability of glucose, although the cause of this is unclear.

Example 2

Physical activity is recommended for all individuals and proven to decrease the risk of cardiovascular disease, cancer, hypertension, obesity, depression, and osteoporosis. In addition to its general health benefits, physical activity is also associated with increased longevity and with decreased risk of diabetes-related complications, such as retinopathy and neuropathy. Given the role of physical activity in improving health and preventing the aforementioned comorbidities, it is alarming that still more than 60% of the population with T1D remains sedentary.

Despite well-documented guidelines for physical activity related BG management and advancements in technologies facilitating glycemic control, physical activity remains one of the main impediments to optimizing glycemic control in T1D. The current guidelines provide strategies based on the intensity and duration of the physical activity as well as the metabolic state (e.g., glucose and insulin levels) of the patient at the time of a structured physical activity bout. The performance of these strategies is limited to the accuracy of the evaluation of these factors by the patient. The rising availability of off-the-shelf physical activity trackers offers a more objective alternative to self-evaluation. Recent studies show that the use of physical activity signals from these trackers are effective in detecting physical activity and improving glycemic control in closed-loop control systems.

Beyond structured physical activity, even short episodes of walking accumulated throughout a day have a significant impact on glycemic control. Therefore, glycemic control in people with T1D may improve when all daily physical activity is considered in the design and adjustment of insulin therapy.

Figure 8:
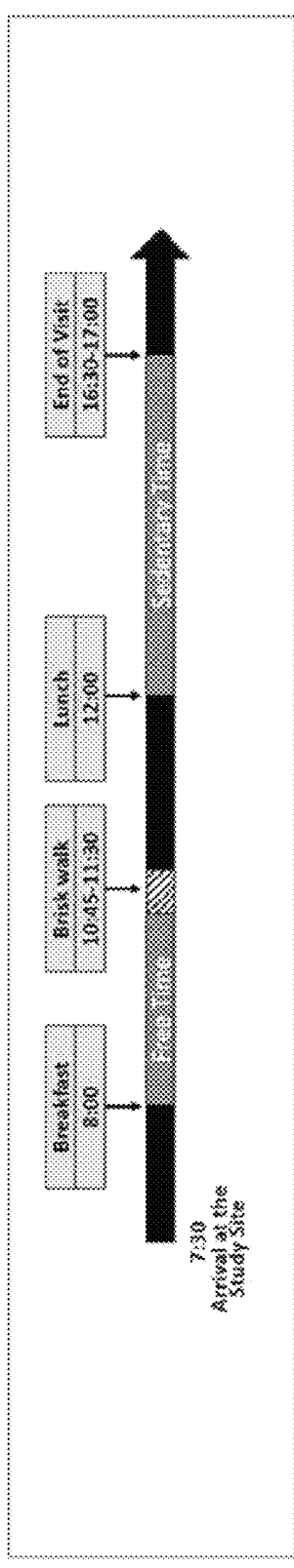
FIG. 8 shows a timeline of outpatient study visits.

FIG. 8 shows a timeline of outpatient study visits. In this study, mealtime insulin treatment for physical activities are adjusted beyond the routine of individuals. The motivation of is to facilitate physical activity related glucose management in a patient-specific manner and based on objectively measured physical activity. Results from a pilot study designed to assess the safety and feasibility of this method are presented—using step count as a ubiquitously available physical activity indicator—to adjust mealtime insulin and thereby improve protection against hypoglycemia, following a walking physical activity bout. To do so, post-meal glycemic control performance of the method is compared to the standard therapy in a randomized crossover clinical trial.

Study Design and Methods

Participants

Fifteen insulin pump users with T1D participated in a randomized, crossover study. The inclusion criteria were duration of diabetes of at least one year, using an insulin pump for at least six months, using defined parameters for calculating meal, and correction insulin boluses, and willingness to maintain a consistent physical activity regimen during the data collection period. Exclusion criteria were pregnancy, diabetic ketoacidosis or severe hypoglycemia in the 6 months prior to enrollment, use of non-insulin medications intended to lower glucose (e.g., GLP-1 agonists, metformin), current use of a clearly defined method for insulin bolus adjustment to compensate for significant physical activity, inability to be physically active for more than 30 minutes per day, or current enrollment in another intervention clinical trial. The Institutional Review Board at the University of Virginia approved the study protocol and consent form. Informed consent was obtained from every participant.

Protocol

The study involved of a free-living data collection period followed by two outpatient day-long supervised visits conducted at the University of Virginia Center for Diabetes Technology, following a randomized crossover design (clinicaltrials.gov: NCT03394352). During data collection period, records of CGM, insulin, meal, and physical activity were collected for more than 20 days under participants' free-living conditions. CGM data were obtained via Dexcom G6 (Dexcom, San Diego, CA) and physical activity data were collected via Fitbit Charge 2 (Fitbit, San Francisco, CA) wristband. Subjects were instructed to enter any consumed carbohydrates into the bolus calculator of their pumps or the CGM mobile application.

The 2 outpatient supervised visits had the same timeline (see FIG. 8) and were separated by at least 2 days to allow wash-out. These visits started at 7:30 am upon the participants' arrival at the study unit. After arrival, each participant's basal insulin rate was set to their regular basal insulin profiles, and no temporary basal rates were used during the visits. Around 8:00 AM, a mixed-meal with 24 g of carbohydrates was provided for breakfast. In both visits, breakfast boluses were calculated according to the participants' usual treatment parameters and with a target glucose of 110 mg/dl. Until 10:45 AM, participants were given free time with no constraints on their activities during their first visit. In their second visit, they were asked to repeat physical activity behavior similar to their previous visit. At 10:45 AM, the physical activity session started. Participants walked briskly at a steady pace on a track for an assigned time of either 30 or 45 minutes. This duration was determined for each participant in a manner to exceed their habitual accumulated physical activity by lunchtime. At noon, lunch was provided with a carbohydrate content matching each participant's routine lunch. Participants' habitual accumulated physical activity by lunch-time and routine lunch carbohydrate contents were derived from their data collected during the free-living data collection phase. Each participant had the same breakfast and lunch in both visits to control for the meal effect. Participants selected their own meal without any limitation on the composition except for the amount of the carbohydrates.

In the control visit, insulin boluses for lunch were calculated according to the standard therapy (ST). In the experimental visit, these boluses were adjusted according to the physical activity informed bolus method. The adjustment was limited to 50% of the standard meal bolus. This was an empirically chosen safety layer for this pilot study. Following lunch, participants were asked to limit their physical activity to the minimum possible until the end of both study visits in order to observe the post-prandial glycemic control performance with minimal distortion. Hypoglycemia events were treated with carbohydrate administration at an amount determined by the study physician and were recorded at all times. Both study visits ended after the post-lunch glycemic excursions were completed, approximately 4.5 to 5 hours after lunch. At the end of each study visit, participants' CGM, insulin pump, and physical activity tracker data were downloaded for the visit and were used in the analyses disclosed herein.

Algorithm Description

The standard therapy bolus for pre-meal insulin dose calculation in T1D has three components: the amount required to compensate for the carbohydrates ingested in the meal, the amount required to correct for any current elevated glucose level at the time of the meal, and the insulin on board (IOB) that is the active insulin from previous injections. The resulting bolus calculation formula is as follows:

$$ST \text{ Bolus} = \frac{CHO \text{ Intake}}{CR} + \frac{BG - BG_{target}}{CF} - IOB$$

where CHO Intake is the amount of ingested carbohydrates in the meal, CR is the carbohydrate-to-insulin ratio (g/U), $BG_{target}$ is the target BG value, CF is the BG correction factor (mg/dL/U) (or a measure of insulin sensitivity), BG is the self-monitored BG value or CGM reading at the time of the meal, and IOB is the insulin on board from previous basal and correction insulin injections.

The IOB component is an important element to account for the lasting impact on BG of previously administered insulin. A similarity between the effect of physical activity and insulin is rooted in the fact that the glycemic impact of physical activity is also prolonged. Therefore, a physical activity informed insulin bolus method is devised that augments the standard therapy bolus formula with a physical activity component inspired by the concept of JOB. This component corresponds to the amount of insulin required to compensate for estimated glycemic disturbances related to previously performed physical activity. The modulation relies on a wearable activity tracker based calculation of accumulated physical activity through a weighted sum of the historical steps taken within the previous 12 hours. The resulting metric, AOB, characterizes the accumulated physical activity that is still actively impacting glucose uptake. Once the AOB is obtained at the time of the meal bolus, the physical activity informed boluses can be calculated as follows:

$$PA \text{ informed bolus} = ST \text{ Bolus} - \frac{AOB_{d,m} - AOB_{profile,m}}{AF}$$

The $AOB_{d,m}$ is the AOB calculated for the meal m consumed on day d. $AOB_{profile,m}$ is the profile that captures the routine daily accumulated physical activity of a participant around a selected standard meal m such as breakfast, lunch or dinner. Note that $AOB_{profile,m}$ serves as a reference for the regular accumulated physical activity of the patient at the selected mealtime for which the average treatment is designed. Deviations from the regular physical activity are expected to cause changes in the insulin needs and the physical activity informed bolus is designed to modulate the insulin dose accordingly. The patient-specific bolus correction parameter, activity factor (AF), translates the anticipated glycemic change generated by the physical activity deviations into insulin units with a similar impact. Thus, the AF and the formula above can be used to modify the disturbance profiles, augment the probability analysis of the predictive model, and/or be modified by the anticipated profiles themselves. For example, AF could be used as a multiplier on the disturbance profile to adjust to differences between the amount of activity observed vs the amount of activity in the anticipated profile (translating amount of activity into insulin amounts). Another example of use could be that the $AOB_{d,m} - AOB_{profile,m}$ quantity is used as in determining the distance between data and profile (instead of the direct activity tracker measurements). Finally, the PA informed bolus could use a variety of profiles (indexed by i below), informed by the matching procedure described above through a weight pi (derived from the matching distance). In this case the bolus may be calculated as:

$$PA \text{ informed bolus} = ST \text{ Bolus} - \sum_i p_i \frac{AOB_{d,m} - AOB_{profile_i,m}}{AF}$$

The direction of the resulting bolus adjustment depends on whether $AOB_{d,m}$ is greater or smaller than $AOB_{profile,m}$. Its magnitude is a function of the amount of the deviation from the profile and the value of the AF. The optimized meal bolus parameters, CR and AF, used in physical activity informed bolus calculations are obtained for each participant following the steps provided in the supplementary document and detailed in Ozaslan et al.

In the calculation of the lunchtime bolus, optimized CRs were used in both outpatient visits while AF was used to correct for the previous physical activity only in the experimental visit.

Outcomes

The primary outcome measure was the time spent in hypoglycemia during the post-prandial window following lunch. Secondary outcomes were the time spent in target range (70-180 mg/dL), low blood glucose index (LBGI), and high blood glucose index (HBGI). The paired Wilcoxon rank test was used to statistically compare both the hypoglycemia counts and LBGI due to their non-Gaussian distributions. The paired t test was used to compare the percentage of time spent in the target range and the HBGI metrics. To assess the hypoglycemia mitigation potential of the two bolus methods, the rate of glucose change in the first 2 hours in the post-prandial period were reported. This time window corresponds to the phase that the rate of physical activity-induced glucose uptake is maximum. For this assessment, linear mixed-effect analysis with covariates of categorical study visit variable and continuous lunchtime BG variable were used. In the models, the hypoglycemia treatments administered from 1 hour prior to lunch until the end of the post-prandial window is controlled. Participant effect is accounted for as a random effect.

Results

Fifteen subjects (6 men and 9 women) completed the study. Participant demographic characteristics, expressed in means±standard deviation, are presented in Table 5.

TABLE 5

| Demographic Characteristics of Study Participants. | | | | |
|---|---|---|---|---|
| | Mean | SD | Minimum | Maximum |
| Age (years) | 47.8 | 10.6 | 23 | 60 |
| Height (cm) | 168.3 | 10.1 | 154 | 181 |
| Weight (kg) | 77.7 | 16.9 | 53.3 | 110 |
| BMI (kg/m²) | 27.5 | 6.2 | 21.6 | 44.1 |
| HbA$_{1c}$ (%) | 7.2 | 0.9 | 6.1 | 9.2 |
| Type 1 diabetes duration (years) | 26.7 | 13.5 | 2 | 47 |

For four participants, CR optimization for lunch was not feasible (e.g., lack of meal bolus between 11:00 AM and 2:00 PM on most days). Therefore, these participants' original lunchtime CR during both study visits were used. For six participants, the optimization failed in finding an optimum AF within the optimization boundaries. In these cases, 2200 accumulated steps as an approximated average AF was used. In cases where CR optimization was feasible, it led to a 2%±18% change from the participant's original CR with no statistically significant difference (original: 10.6±2.7 g/U, optimized: 11±3.8 g/U, P=0.64). The average of optimum AFs, computed from the 9 patients that the optimization was feasible for, was 2926±1267 accumulated steps/U.

During the experimental visit, physical activity related bolus reduction was on average 28%±15% of the total bolus. Participants' glucose values at lunchtime were similar between study visits (control: 126±41 mg/dL, experimental:

127±35 mg/dL, P=0.94). There was no significant difference between visits for the AOB at lunchtime (control: 5438±1048 accumulated steps, experimental: 5258±969 accumulated steps, P=0.32). Nine hypoglycemia instances occurred within the previous hour of lunch (five in experimental, four in the control admission), and were treated with rescue carbohydrates. Hypoglycemia occurrence was rather rare in the post-lunch period in both visits; glucose levels below 70 mg/dL occurred in only 3 out of 30 observations (1 in the experimental, and 2 in the control visit) and treated with 25.7±5.1 g of rescue carbohydrates. As a result, there was no statistically significant difference in the percentage of time spent in hypoglycemia between visits (median 16:30 PM during the study visit. The glucose values in the afternoon had a higher variation compared to the morning since glucose levels were managed by the study physician in the morning to bring them to a safe glucose range for physical activity. Furthermore, the range of meals taken for lunch are wider than the ones for breakfast.

Figure 10:
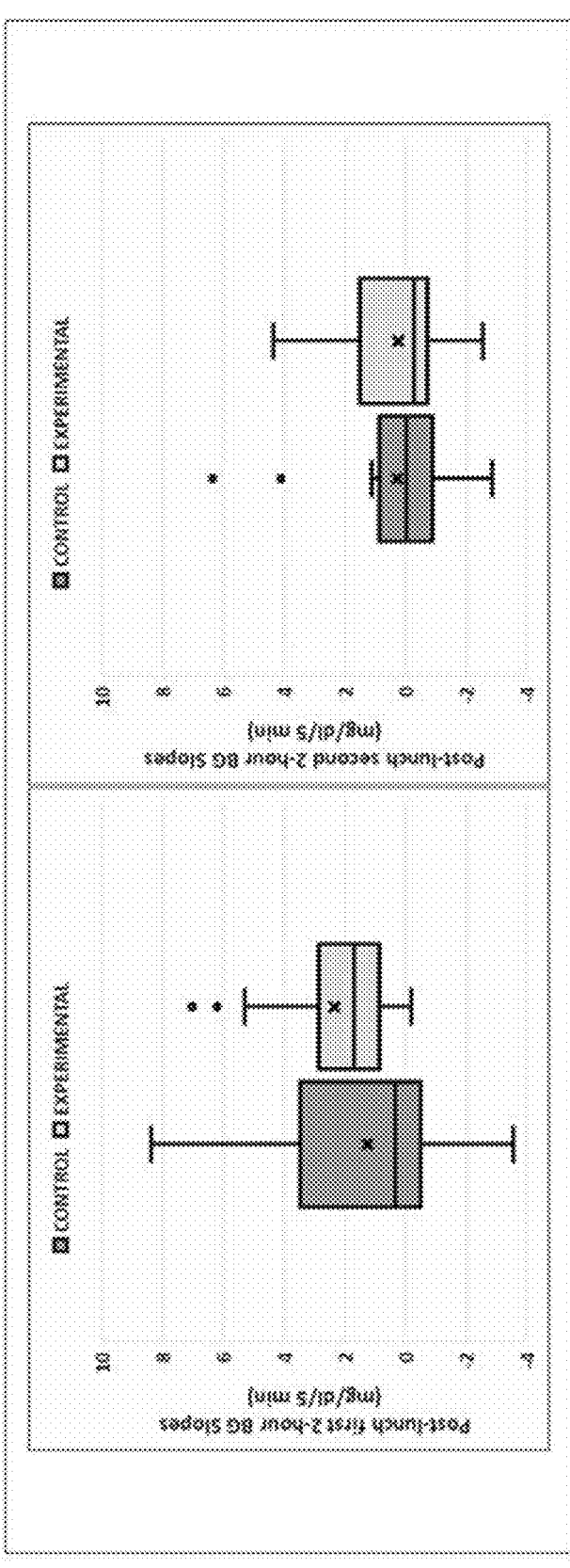
FIG. 10 shows boxplot representation of post-lunch CGM slope trends in study visits separated for the observation in the first 2 hours (left) and in the second 2 hours (right) following the lunch means.

CGM slopes for the first two-hour phase were negative in 40% of the observations in the control visit and this was reduced to 7% in the experimental visit (see FIG. 10). FIG. 10 shows a boxplot representation of post-lunch CGM slope trends in study visits separated for the observation in the first 2 hours (left) and in the second 2 hours (right) following the lunch means.

TABLE 6

Regression Analysis Results on Post-Lunch CGM Slope Trends in the First 2 Hours (Left) and in the Second 2 Hours (Right) Following the Lunch Meals.

| Post−lunch [0 h, 2 h]  Slope analysis | Value ± SE | P-value | Post−lunch [2 h, 4h]  Slope analysis | Value ± SE | P-value |
|---|---|---|---|---|---|
| Intercept | 3.9 ± 1.49 | .04* | Intercept | 0.16 ± 1.48 | .917 |
| $CGM_{lunchtime}$ | −0.02 ± 0.01 | .032 | $CGM_{lunchtime}$ | −0.002 ± 0.01 | .853 |
| Experimental visit | 1.2 ± 0.5 | .032* | Experimental visit | 0.2 ± 0.52 | .712 |

[IQR], control: 0 [0]%, experimental: 0 [0]% P=1). The percentage of time spent in the target range was lower with physical activity informed boluses (control: 77%±27% experimental: 59%±31% P=0.03). However, no significant difference was observed for LBGI (median [IQR], control: 0 [0.03], experimental: 0 [0.02], P=0.62) or HBGI (control: 0.82±0.8, experimental: 0.78±0.6, P=0.83) in the post-lunch period.

Overall, the afternoon physical activity, as measured by total number of steps, was significantly lower during the study visits compared to the participants' routine physical activity extracted from the data collection period (control: 1095±451 steps, experimental: 1288±702 steps, data collection: 2555±1618 steps, with P<0.01 for both control vs data collection and experimental vs data collection afternoon physical activity). No significant difference was observed between the total number of steps that participants took in the afternoon portion of control vs experimental visits (P=0.18).

Figure 9:
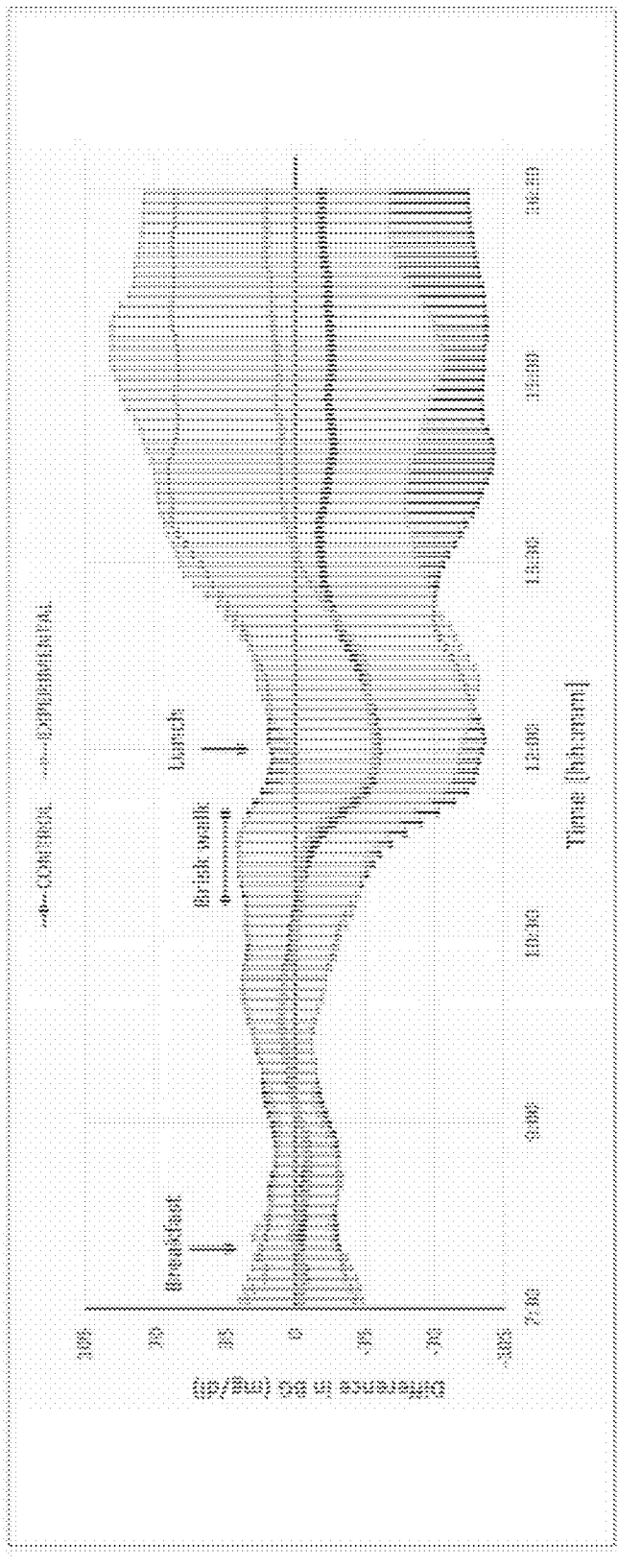
FIG. 9 shows a change in CGM in the control (dark grey) and the experimental (light grey) visits.

As indicated in FIG. 9, on average, standard therapy bolus yielded a late post-prandial glucose below the morning average glucose while the physical activity informed bolus yielded a higher glucose than this reference; albeit statistically not significant ($\Delta CGM_{reference}$ control: −16±74 mg/dL, $\Delta CGM_{reference}$ experimental: 10±68 mg/dL, P=0.09). The differences in the direction and magnitude of glucose change in the early and late phases of post-lunch glycemic excursion are evaluated through CGM slopes in linear mixed effects regression analyses with the results provided in Table 6. While study visit was a significant factor associated with the CGM trend in the first two hours following bolus injection (P=0.032), no significant difference was observed in the CGM trend in the late post-lunch phase (between second and fourth hours after lunch) between visits (P=0.71).

FIG. 9 shows change in CGM in the control (dark grey) and the experimental (light grey) visits. The reference CGM value for each visit and participant is their average morning CGM calculated from CGM readings between 7:30 AM and 10:45 AM for the related visit. All values are then obtained by subtracting the subject and visit specific reference CGM values from the observed CGM readings from 7:30 AM until Discussion One goal of this pilot feasibility study was to assess whether step-count based physical activity information could be used to enhance hypoglycemia protection of a meal bolus following a brisk walking session. Negative CGM slopes in the early post-prandial phase support the need for formal incorporation of previous physical activity into insulin bolus calculations. While the physical activity-informed bolus method was able to successfully compensate for the decrease in glucose levels, results imply that it might be too conservative against the risk of hypoglycemia since it yielded an average glucose trend higher than the computed participant-specific reference glucose averages in the experimental arm of the study. In other words, results showed that meal treatment with the standard care following a walking physical activity session led to below the reference glucose levels, implying an increased risk for hypoglycemia, albeit not as much as anticipated. Despite full bolus administration in the control session, a rather low rate of hypoglycemia and higher time in the target range compared to the experimental session was observed. More specifically, only 3 instances of post-lunch hypoglycemia occurred during the trial. As such, participants indeed benefited from the walking exercise in terms of the time spent in target range. These findings suggest that additional factors should be considered while adjusting the insulin bolus for physical activity. Along this study, factors attenuating the activity-induced increase in the glucose uptake may include the high protein and fat content of the breakfast, which was designed for having minimum IOB at the time of the walking exercise. Additionally, the afternoon portion of the study incorporated minimum physical activity that was significantly lower than the participants' routine afternoon physical activity upon which the treatment parameters were prescribed and optimized. These conditions, along with the unbolused rescue carbohydrates around lunch, likely led to higher glucose values than expected.

The variable "Experimental Visit" in the regression models is categorical and the coefficients associated with it show marginal difference in the slopes in experimental compared to the control visit.

Three aspects of the approach taken in this paper that are worth further examination. First, physical activity on board is computed via a convolution with a reference signal. Different reference signal values may affect the outcomes of the bolus decisions. It can be hypothesized that, based on the mathematical intuition, if the reference signal approximates the decreasing nature of the effect of physical activity on blood glucose well enough, the corresponding adjustment decisions are valid for the intended purpose. Second, the literature on the prolonged glycemic effect of physical activity in individuals with T1D is limited. For instance, the reference study demonstrated a biphasic change in glucose uptake in adolescents after an exercise bout performed by adolescents late in the day. However, it was shown in Davey et al that when the exercise bout was at mid-day, the change in the glucose uptake was rather stable from one hour after the exercise until 11 hours. Similar studies in adults at differing times of the day and for different physical activity modalities could provide more accurate signals for the method. The third aspect is the fact that physical activity has a longer horizon of effect (12 hours) than the one for insulin injections (5 hours). This discrepancy translates to possible over-reduction of insulin dose for the performed physical activity as the AOB predictions anticipate further blood glucose decrease for hours after the insulin was used. Additionally, the glycemic outcomes for up to five hours after the end of the physical activity session were observed, and about half of the total glycemic impact from the performed physical activity was anticipated to occur in the hours after our observation window, based on McMahon et al.'s study. One possible way to reconcile this discrepancy is to make physical activity corrections to compensate only for the changes anticipated to occur within the duration of insulin action.

It is noteworthy that in the first 2 hours of post-lunch phase, standard boluses yielded a higher tendency toward decreasing glucose compared to the physical activity informed boluses. These results are compatible with the current knowledge of an increased glucose uptake up to 2 hours following moderate-intensity physical activity.

In conclusion, this pilot study presents early safety and feasibility data of a novel method to quantify physical activity via a ubiquitously available measurement, step count, and utilize this quantity to modulate prandial insulin boluses. This method can be adapted to different physical activity indicators, physical activity accumulation methods, as well as the changing baseline physical activity behavior of individuals through the parameters AOB and AF. The results suggest that person-specific treatment adjustments through step-based quantifications of physical activity are safe, feasible, and have potential in mitigating physical activity-induced BG decrease in the early post-meal window in people with T1D.

Example 2 demonstrates that physical activity can cause glucose fluctuations both during and after it is performed, leading to hurdles in optimal insulin dosing in people with type 1 diabetes (T1D). The pilot clinical trial assessed the safety and feasibility of a physical activity-informed meal-time insulin bolus advisor that adjusts the meal bolus according to previous physical activity, based on step count data collected through an off-the-shelf physical activity tracker. Fifteen adults with T1D, each using a continuous glucose monitor (CGM) and an insulin pump with carbohydrate counting, completed two randomized crossover daily visits. Participants performed a 30 to 45-minute brisk walk before lunch and lunchtime insulin boluses were calculated based on either their standard therapy (ST) or the physical activity-informed bolus method. Post-lunch glycemic excursions were assessed using CGM readings. There was no significant difference between visits in the time spent in hypoglycemia in the post-lunch period (median [IQR] standard: 0 [0]% vs physical activity-informed: 0 [0]%, P=NS). Standard therapy bolus yielded a higher time spent in 70 to 180 mg/dL target range (mean±standard: 77%±27% vs physical activity-informed: 59%±31%, P=0.03); yet, it was associated with a steeper negative slope in the early postprandial phase (P=0.032). Thus, use of step count to adjust mealtime insulin following a walking bout has proved to be safe and feasible in a cohort of 15 T1D subjects. Physical activity-informed insulin dosing of meals eaten soon after a walking bout has a potential of mitigating physical activity related glucose reduction in the early postprandial phase.

Examples 1 and 2 demonstrate that an individualized multistage model predictive control (MS-MPC) algorithm for BG stabilization and improved postprandial BG control for people with type 1 diabetes (T1D) with consistent meal patterns is achievable. The multistage formulation can utilize different meal patterns as disturbance realizations entering the glucose-insulin system, then can assess the best possible control input among all of the probable scenarios. The disturbance realizations, in the form of glucose rate of appearance traces, can be estimated by using meal records (time and carbohydrate amount) as the input into an individualized oral model. Meal signatures can then be clustered with the k-medoids algorithm to obtain meal patterns. Two approaches, a hybrid closed-loop (HCL) and fully closed-loop (FCL) MS-MPC were tested and compared with their respective control treatments (hybrid and fully automated MPC, respectively) using the complete in silico adult cohort of the FDA-accepted UVA/Padova metabolic simulator. Results confirm an improvement in both postprandial and overall percent time in 70-180 mg/dl 85.2±15.5 v. 89.6±12.2 and 94.1±6.3 v. 95.7±5.0, respectively, using the HCL approach, and 37.8±15.7 v. 63.4±16.6 and 65.8±12.7 v. 82.2±9.2, using the FCL approach.P In health, the pancreas regulates the production of insulin, which allows for glucose to clear from plasma, and glucagon, which stimulates the liver to release glucose into the blood. In T1D, this precise feedback process is dysregulated. The pancreas does not produce insulin, leading to high blood glucose (BG), also known as hyperglycemia. To prevent this, exogenous insulin must be administered for life to maintain plasma glucose levels within a safe range.

Treatment guidelines suggest that people with T1D calculate an insulin dose at meal times based on carbohydrate counting (CC) and their insulin therapy parameters American Diabetes Association (2016); Tascini et al. (2018). Furthermore, to minimize the effect of ingested carbohydrates on glucose levels, insulin should be ideally administered 15-20 minutes before food Slattery et al. (2018). Results related to how accurate people with T1D are at CC vary from study to study, but there is a consensus that errors in CC are common in real-life. Deeb et al. reported that children and adolescents are only able to make accurate carbohydrate estimations for 67% of meals Deeb et al. (2017). Another study showed that adults with T1D were only able to estimate the carbohydrate content of foods within a 5 gram range of the true amount 44% of the time Meade and Rushton (2016). A survey by Lancaster et al. reported that adolescents with T1D consider CC as a barrier to achieving glycemic control Lancaster et al. (2010).

Postprandial glucose management remains a challenge for conventional artificial pancreas systems (APS). In a hybrid closed-loop (HCL) approach, inaccurate CC and parameters such as carbohydrate ratio (CR) and insulin-to-carbohydrate correction factor (ICF) have a meaningful impact on glucose control since insulin underdose/overdose may arise Bally et al. (2017): Kovatchev et al. (2017). Although promising results regarding fully closed-loop (FCL) systems have been reported, balancing the controller's aggressiveness to mitigate meal-related glucose excursions without increasing the risk of late hypoglycemia remains an open challenge for conventional systems Dassau et al. (2013); Turksoy et al. (2016); Bally et al. (2017); Colmegna et al. (2018); Sanchez-Pena et al. (2018).

Meal anticipation can improve APS postprandial control for both HCL and FCL systems. For example, Hughes et al. approached the issue of the delay between subcutaneous BG measurements and the effect of insulin action, by anticipating meals using a random meal profile Hughes et al. (2011). In silico results from this paper showed that the HCL approach that used meal anticipation and insulin boluses for announced carbohydrates resulted in an attenuated postprandial BG excursion when compared to open-loop control with meal boluses.

FIG. 11 is a block diagram illustrating an example of a machine upon which one or more aspects of embodiments of the present invention can be implemented.

Referring to FIG. 11, an aspect of an embodiment of the present invention includes, but not limited thereto, a system, method, and computer readable medium that provides: a model for informing, determining, or controlling insulin dosage, which illustrates a block diagram of an example machine 1100 upon which one or more embodiments (e.g., discussed methodologies) can be implemented (e.g., run).

Examples of machine 1100 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium (e.g., non-transitory, non-volatile memory) or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time.

For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs)).

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a standalone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine 1100) and software architectures that can be deployed in example embodiments.

In an example, the machine 1100 can operate as a standalone device or the machine 1100 can be connected (e.g., networked) to other machines.

In a networked deployment, the machine 1100 can operate in the capacity of either a server or a client machine in server-client network environments. In an example, machine 1100 can act as a peer machine in peer-to-peer (or other distributed) network environments. The machine 1100 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 1100. Further, while only a single machine 1100 is illustrated, the term "machine" shall also be taken to include any collection of machines that individually or jointly execute a set (or multiple sets) of instructions to perform any one or more of the methodologies discussed herein.

Example machine (e.g., computer system) 1100 can include a processor 1102 (e.g., a central processing unit (CPU), a graphics processing unit (GPU) or both), a main memory 1104 and a static memory 1106, some or all of which can communicate with each other via a bus 1108. The machine 1100 can further include a display unit 1110, an alphanumeric input device 111 (e.g., a keyboard), and a user interface (UI) navigation device 1114 (e.g., a mouse). In an example, the display unit 1110, input device 1117 and UI navigation device 1114 can be a touch screen display. The machine 1100 can additionally include a storage device (e.g., drive unit) 1116, a signal generation device 1118 (e.g., a speaker), a network interface device 1120, and one or more sensors 1121, such as a global positioning system (GPS) sensor, compass, accelerometer, or other sensor.

The storage device 1116 can include a machine readable medium 1122 on which is stored one or more sets of data structures or instructions 1124 (e.g., software) embodying or utilized by any one or more of the methodologies or functions described herein. The instructions 1124 can also reside, completely or at least partially, within the main memory 1104, within static memory 1106, or within the processor 1102 during execution thereof by the machine 1100. In an example, one or any combination of the processor 1102, the main memory 1104, the static memory 1106, or the storage device 1116 can constitute machine readable media. While the machine readable medium 1122 is illustrated as a single medium, the term "machine readable medium" can include a single medium or multiple media (e.g., a centralized or distributed database, and/or associated caches and servers) that configured to store the one or more instructions 1124. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 1124 can further be transmitted or received over a communications network 1126 using a transmission medium via the network interface device 1120 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

It will be understood that modifications to the embodiments disclosed herein can be made to meet a particular set of design criteria. For instance, any component or feature can be any suitable number or type of each to meet a particular objective. Therefore, while certain exemplary embodiments of the system, apparatus, and methods of making and using the same disclosed herein have been discussed and illustrated, it is to be distinctly understood that the invention is not limited thereto but can be otherwise variously embodied and practiced within the scope of the following claims.

It will be appreciated that some components, features, and/or configurations can be described in connection with only one particular embodiment, but these same components, features, and/or configurations can be applied or used with many other embodiments and should be considered applicable to the other embodiments, unless stated otherwise or unless such a component, feature, and/or configuration is technically impossible to use with the other embodiment. Thus, the components, features, and/or configurations of the various embodiments can be combined together in any manner and such combinations are expressly contemplated and disclosed by this statement.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein. Additionally, the disclosure of a range of values is a disclosure of every numerical value within that range, including the end points.

The following references are incorporated herein by reference in their entireties.

1. V. Gingras, N. Taleb, A. Roy-Fleming, L. Legault, and R. Rabasa-Lhoret, "The challenges of achieving post-prandial glucose control using closed-loop systems in patients with type 1 diabetes," Diabetes, Obes. Metab., vol. 20, no. 2, pp. 245-256, February 2018, doi: 10.1111/dom.13052.

2. J. P. Corbett, P. Colmegna, J. Garcia-Tirado, and M. D. Breton, "Anticipating Meals with Behavioral Profiles in an Artificial Pancreas System—An Informed Multistage Model Predictive Control Approach," IFAC-PapersOnLine, vol. 53, no. 2, pp. 16305-16310, January 2020, doi: 10.1016/j.ifacol.2020.12.652.

3. R. A. Harvey et al., "Clinical evaluation of an automated artificial pancreas using zone-model predictive control and health monitoring system," Diabetes Technol. Ther., vol. 16, no. 6, pp. 348-357, June 2014, doi: 10.1089/dia.2013.0231.

4. G. P. Forlenza et al., "Fully Closed-Loop Multiple Model Probabilistic Predictive Controller Artificial Pancreas Performance in Adolescents and Adults in a Supervised Hotel Setting," Diabetes Technol. Ther., vol. 20, no. 5, pp. 335-343, May 2018, doi: 10.1089/dia.2017.0424.

5. K. Dovc et al., "Faster Compared with Standard Insulin Aspart during Day-And-Night Fully Closed-Loop Insulin Therapy in Type 1 Diabetes: A Double-Blind Randomized Crossover Trial," Diabetes Care, vol. 43, no. 1, pp. 29-36, January 2020, doi: 10.2337/dc19-0895.

6. H. Blauw, A. J. Onvlee, M. Klaassen, A. C. van Bon, and J. H. DeVries, "Fully Closed Loop Glucose Control With a Bihormonal Artificial Pancreas in Adults With Type 1 Diabetes: An Outpatient, Randomized, Crossover Trial," Diabetes Care, vol. 44, no. 3, pp. 836-838, March 2021, doi: 10.2337/dc20-2106.

7. A. Haidar et al., "Reducing the need for carbohydrate counting in type 1 diabetes using closed-loop automated insulin delivery (artificial pancreas) and empagliflozin: A randomized, controlled, non-inferiority, crossover pilot trial," Diabetes, Obes. Metab., 2021, doi: 10.1111/dom.14335.

8. D. Majdpour et al., "Fully Automated Artificial Pancreas for Adults with Type 1 Diabetes using Multiple Hormones: Exploratory Experiments," Can. J. Diabetes, February 2021, doi: 10.1016/j.jcjd.2021.02.002.

9. J. Garcia-Tirado, J. P. Corbett, D. Boiroux, J. B. Jorgensen, and M. D. Breton, "Closed-loop control with unannounced exercise for adults with type 1 diabetes using the Ensemble Model Predictive Control," J. Process Control, vol. 80, pp. 202-210, August 2019, doi: 10.1016/j.jprocont.2019.05.017.

10. J. F. Garcia-Tirado, P. Colmegna, J. P. Corbett, B. Ozaslan, and M. D. Breton, "Ensemble Model Predictive Control Strategies Can Reduce Exercise Hypoglycemia in Type 1 Diabetes: In Silico Studies," in 2019 American Control Conference (ACC), 2019, vol. 2019-July, pp. 4752-4758, doi: 10.23919/acc.2019.8814728.

11. J. Garcia-Tirado, P. Colmegna, J. P. Corbett, B. Ozaslan, and M. D. Breton, "In Silico Analysis of an Exercise-Safe Artificial Pancreas With Multistage Model Predictive Control and Insulin Safety System," J. Diabetes Sci. Technol., vol. 13, no. 6, 2019, doi: 10.1177/1932296819879084.

12. J. Garcia-Tirado et al., "Anticipation of Historical Exercise Patterns by a Novel Artificial Pancreas System Reduces Hypoglycemia During and After Moderate-Intensity Physical Activity in People with Type 1 Diabetes," Diabetes Technol. Ther., vol. 23, no. 4, December 2020, doi: 10.1089/dia.2020.0516.

13. B. Ozaslan et al., "Safety and Feasibility Evaluation of Step Count Informed Meal Boluses in Type 1 Diabetes: A Pilot Study," J. Diabetes Sci. Technol., p. 193229682199791, April 2021, doi: 10.1177/1932296821997917.

14. C. Ellingsen et al., "Safety constraints in an artificial pancreatic β cell: An implementation of model predictive control with insulin on board," J. Diabetes Sci. Technol., vol. 3, no. 3, pp. 536-544, 2009, doi: 10.1177/193229680900300319.

15. R. W. Hamming, "Error Detecting and Error Correcting Codes," Bell Syst. Tech. J., vol. 29, no. 2, pp. 147-160, April 1950, doi: 10.1002/j.1538-7305.1950.tb00463.x.

16. S. P. Lloyd, "Least Squares Quantization in PCM," 1982. Accessed: Aug. 15, 2019. [Online]. Available: https://sites.cs.ucsb.edu/~veronika/MAE/kmeans_L-Loyd_Least_Squares_Quantization_i n_PCM.pdf.

17. T. Caliñiski and J. Harabasz, "A Dendrite Method Foe Cluster Analysis," Commun. Stat., vol. 3, no. 1, pp. 1-27, 1974, doi: 10.1080/03610927408827101.

18. S. D. Patek, "Open-loop feedback control under multiple disturbance function hypotheses," 2010, doi: 10.1109/CDC.2010.5717476.

19. S. A. Brown et al., "Six-Month Randomized, Multi-center Trial of Closed-Loop Control in Type 1 Diabetes," N. Engl. J. Med., vol. 381, no. 18, pp. 1707-1717, October 2019, doi: 10.1056/NEJMoa1907863.

20. R. Visentin et al., "The UVA/Padova Type 1 Diabetes Simulator Goes From Single Meal to Single Day," J. Diabetes Sci. Technol., vol. 0, no. 0, pp. 1-9, 2018, doi: 10.1177/1932296818757747.

21. D. M. Maahs et al., "Outcome measures for artificial pancreas clinical trials: A consensus report," Diabetes Care, vol. 39, no. 7, pp. 1175-1179, July 2016, doi: 10.2337/dc15-2716.

22. J. W. White, A. Rassweiler, J. F. Samhouri, A. C. Stier, and C. White, "Ecologists should not use statistical significance tests to interpret simulation model results," Oikos, vol. 123, no. 4, pp. 385-388, April 2014, doi: 10.1111/j.1600-0706.2013.01073.x.

23. Warburton D E R, Nicol C W, Bredin S S D. Health benefits of physical activity: the evidence. Can Med Assoc J. 2006; 174(6):801-809.

24. Paffenbarger R S, Hyde R, Wing A L, Hsieh C. Physical activity, all-cause mortality, and longevity of college alumni. N Engl J Med. 1986; 314(10):605-613.

25. Balducci S, Iacobellis G, Parisi L, et al. Exercise training can modify the natural history of diabetic peripheral neuropathy. J Diabetes Complications 2006; 20(4):216-223.

26. Bohn B, Herbst A, Pfeifer M, et al. Impact of physical activity on glycemic control and prevalence of cardio-vascular risk factors in adults with type 1 diabetes: a cross-sectional multicenter study of 18,028 patients. Diabetes Care. 2015; 38(8):1536-1543.

27. Brazeau A-S, Rabasa-Lhoret R, Strychar I, Mircescu H. Barriers to physical activity among patients with type 1 diabetes. Diabetes Care. 2008; 31(11):2108-2109.

28. Riddell M C, Gallen I W, Smart C E, et al. Exercise management in type 1 diabetes: a consensus statement. Lancet Diabetes Endocrinol. 2017; 5(5):377-390.

29. Colberg S R, Sigal R J, Yardley J E, et al. Physical activity/exercise and diabetes: a position statement of the American Diabetes Association. Diabetes Care. 2016; 39(11):2065-2079.

30. Cinar A. Multivariable adaptive artificial pancreas system in type 1 diabetes. Curr Diab Rep. 2017; 17(10):88.

31. Riddell M C, Zaharieva D P, Yavelberg L, Cinar A, Jamnik V K. Exercise and the development of the artificial pancreas: one of the more difficult series of hurdles. J Diabetes Sci Technol. 2015; 9(6):1217-1226.

32. DeBoer M D, Cherriavvsky D R, Topchyan K, Kovatchev B P, Francis G L, Breton M D. Heart rate informed artificial pancreas system enhances glycemic control during exercise in adolescents with T1D. Pediatr Diabetes. 2017; 18(7):540-546.

33. Breton M D, Brown S A, Karvetski C H, et al. Adding heart rate signal to a control-to-range artificial pancreas system improves the protection against hypoglycemia during exercise in type 1 diabetes. Diabetes Technol Ther. 2014; 16(8):506-511.

34. Turksoy K, Bayrak E S, Quinn L, Littlejohn E, Cinar A. Multivariable adaptive closed-loop control of an artificial pancreas without meal and activity announcement. Diabetes Technol Ther. 2013; 15(5):386-400.

35. Garcia-Tirado J, Brown S A, Laichuthai N, et al. Anticipation of historical exercise patterns by a novel artificial pancreas system reduces hypoglycemia during and after moderate-intensity physical activity in people with type 1 diabetes. Diabetes Technol Ther. Published online Dec. 1, 2020. doi:10.1089/dia.2020.0516

36. Dunstan D W, Kingwell B A, Larsen R, et al. Breaking up prolonged sitting reduces postprandial glucose and insulin responses. Diabetes Care. 2012; 35(5):976-983.

37. Bailey D P, Locke C D. Breaking up prolonged sitting with light-intensity walking improves postprandial glycemia, but breaking up sitting with standing does not. J Sci Med Sport. 2015; 18(3):294-298.

38. Peddie M C, Bone J L, Rehrer N J, Skeaff C M, Gray A R, Perry T L. Breaking prolonged sitting reduces postprandial glycemia in healthy, normal-weight adults: a randomized crossover trial. Am J Clin Nutr. 2013; 98(2):358-366.

39. Manohar C, Levine J A, Nandy D K, et al. The effect of walking on postprandial glycemic excursion in patients with type 1 diabetes and healthy people. Diabetes Care. 2012; 35(12):2493-2499.

40. Ozaslan B, Patek S D, Breton M D. Impact of daily physical activity as measured by commonly available wearables on meal time glucose control in type 1 diabetes. Diabetes Technol Ther. 2020; 22(10):742-748.

41. Cappon G, Marturano F, Vettoretti M, Facchinetti A, Sparacino G. In silico assessment of literature insulin bolus calculation methods accounting for glucose rate of change. J Diabetes Sci Technol. 2019; 13(1):103-110.

42. Swan K L, Dziura J D, Steil G M, et al. Effect of age of infusion site and type of rapid-acting analog on pharmacodynamic parameters of insulin boluses in youth with type 1 diabetes receiving insulin pump therapy. Diabetes Care. 2009; 32(2):240-244.

43. McMahon S K, Ferreira L D, Ratnam N, et al. Glucose requirements to maintain euglycemia after moderate-intensity afternoon exercise in adolescents with type 1 diabetes are increased in a biphasic manner. J Clin Endocrinol Metab. 2007; 92(3):963-968.

44. Ozaslan B, Fabris C, Patek S D, Breton M. Automatically accounting for physical activity in insulin dosing for type 1 diabetes. Comput Methods Programs Biomed. Published online Sep. 21, 2020. doi:10.1016/j.cmpb.2020.105757

45. Davey R J, Howe W, Paramalingam N, et al. The effect of mid-day moderate-intensity exercise on postexercise hypoglycemia risk in individuals with type 1 diabetes. J Clin Endocrinol Metab. 2013; 98(7):2908-2914.

What is claimed is:

1. A system for informing, determining, or controlling insulin dosage, the system comprising:
   a processor; and
   memory including instructions to cause the processor to:
      generate plural disturbance profiles, each disturbance profile being a data representation based on historical patient data pertaining to a deviation from a threshold blood glucose level;
      receive current patient data;
      wherein the current patient data and the historical patient data includes any data indicative of a patient characteristic;
      apply a predictive model, wherein:
         the processor is configured by the instructions to compare the current patient data to at least one disturbance profile; and
         the processor is configured by the instructions to assess the likelihood of a disturbance profile of the plural disturbance profiles being an anticipated disturbance profile via probability analysis, the anticipated disturbance profile being a disturbance profile that is determined to match with the current patient data based on the probability analysis;
      determine an insulin dose amount based on the anticipated disturbance profile, the current patient data, previous insulin dose amount data, and a total daily insulin (TDI) for the patient; and
      output a signal representative of the insulin dose amount to a device configured for monitoring, influencing, and/or administering insulin levels in the patient.

2. The system of claim 1, wherein:
   the plural disturbance profiles and/or the predictive model is stored in the memory; or the plural disturbance profiles and/or the predictive model is stored in a memory external to the processor, and the processor is configured to be in communication with the external memory.

3. The system of claim 1, wherein:

the processor is configured by the instructions to compare the current patient data to at least one disturbance profile continuously, periodically, or at a predetermined time.

4. The system of claim 3, wherein:

the processor is configured by the instructions to compare the current patient data to at least one disturbance profile every five minutes.

5. The system of claim 1, wherein:

the historical patient data includes a glucose measurement, meal intake data, a physical activity measurement, and/or insulin injection data; and the current patient data includes a glucose measurement, meal intake data, a physical activity measurement, and/or insulin injection data.

6. The system of claim 5, wherein:

the deviation from the threshold blood glucose level for the disturbance profile is an occurrence of a blood glucose level caused by physical activity and/or meal activity that increases a risk of hyperglycemia and/or hypoglycemia.

7. The system of claim 6, wherein:

the physical activity and/or meal activity includes physical activity and/or meal activity exhibited by the patient that deviates from an average behavior related to physical activity and/or meal activity.

8. The system of claim 7, wherein:

the physical activity and/or meal activity that increases a risk of hyperglycemia and/or hypoglycemia is identified via logistical regression.

9. The system of claim 8, wherein:

the historical patient data include data that pertains to more than one day; and clustering is used to group days having similar deviations from threshold blood glucose levels.

10. The system of claim 1, wherein the instructions cause the processor to:

update at least one disturbance profile and/or create a new disturbance profile based on current patient data.

11. The system of claim 1, in combination with:

a glucose monitoring device, an activity tracking device, and/or a meal tracking device, any one or combination being in communication with the processor and configured to collect or generate the patient data.

12. The combination of claim 11, wherein:

the processor is configured to receive the historical patient data and/or the current patient data from the glucose monitoring device, the activity tracking device, and/or the meal tracking device; and/or the glucose monitoring device, the activity tracking device, and/or the meal tracking device is configured to transmit the historical patient data and/or the current patient data to a data store, wherein the processor is configured to receive the historical patient data and/or the current patient data from the data store.

13. The system of claim 1, in combination with:

an insulin delivery device, a glycemic state monitoring device, a glucose management system, and/or an insulin recommendation system, any one or combination being in communication with the processor and configured to receive the output from the processor.

14. The system of claim 1, wherein the instructions cause the processor to:

configure the output signal as a notification communication causing the device to recommend administration of the insulin dose amount;

configure the output signal as a command signal causing the device to administer the insulin dose amount; and/or configure the output signal as a data point to allow the device to graphically display the insulin dose amount.

15. The system of claim 1, wherein the processor is a control module of an automated insulin dosing system.

16. A system for informing, determining, or controlling insulin dosage, the system comprising:

a processor; and memory including instructions to cause the processor to:

generate plural disturbance profiles, each disturbance profile being a data representation based on historical patient data pertaining to a deviation from a threshold blood glucose level;

receive current patient data;

wherein the current patient data and the historical patient data includes any data indicative of a patient characteristic;

apply a predictive model, wherein:

the processor is configured by the instructions to compare the current patient data to at least one disturbance profile; and the processor is configured by the instructions to assess the likelihood of a disturbance profile of the plural disturbance profiles being an anticipated disturbance profile via probability analysis, the anticipated disturbance profile being a disturbance profile that is determined to match with the current patient data based on the probability analysis;

determine an insulin dose amount based on the anticipated disturbance profile;

modify the insulin dose amount based on the current patient data, previous insulin dose amount data, and a total daily insulin (TDI) for the patient; and output a signal representative of the modified insulin dose amount to a device configured for monitoring, influencing, and/or administering insulin levels in the patient.

17. The system of claim 16, wherein:

the modified insulin dose amount is further based on an insulin on board (IOB) amount.

18. The system of claim 16, wherein the instructions cause the processor to: output a signal representative of the insulin dose amount and the modified insulin dose amount.

19. The system of claim 18, wherein the instructions to cause the processor to:

configure the output signal as a notification communication causing the device to recommend administration of the modified insulin dose amount;

configure the output signal as a command signal causing the device to administer the modified insulin dose amount; and/or configure the output signal as a data point to allow the device to graphically display the modified insulin dose amount.

20. The system of claim 16, wherein the instructions to cause the processor to:

determine a current deviation from the threshold blood glucose level that increases a risk of hyperglycemia and/or hypoglycemia; and

determine the insulin dose amount to be administered based on the current deviation as opposed to being based on the anticipated disturbance profile; and modify the insulin dose amount to account for the current deviation.

21. A computer readable medium having instructions stored thereon that when executed by a processor causes the processor to:

generate plural disturbance profiles, each disturbance profile being a data representation based on historical patient data pertaining to a deviation from a threshold blood glucose level;

receive current patient data;

wherein the current patient data and the historical patient data includes any data indicative of a patient characteristic;

apply a predictive model, wherein:

the instructions cause the processor to compare the current patient data to at least one disturbance profile; and the instructions cause the processor to assess the likelihood of a disturbance profile of the plural disturbance profiles being an anticipated disturbance profile via probability analysis, the anticipated disturbance profile being a disturbance profile that is determined to match with the current patient data based on the probability analysis;

determine an insulin dose amount based on the anticipated disturbance profile, the current patient data, previous insulin dose amount data, and a total daily insulin (TDI) for the patient; and

output a signal representative of the insulin dose amount to a device configured for monitoring, influencing, and/or administering insulin levels in the patient.

22. A method for informing, determining, or controlling insulin dosage, the method comprising:

generating plural disturbance profiles, each disturbance profile being a data representation based on historical patient data pertaining to a deviation from a threshold blood glucose level;

receiving current patient data;

wherein the current patient data and the historical patient data includes any data indicative of a patient characteristic;

applying a predictive model, wherein:

the current patient data is compared to at least one disturbance profile; and probability analysis is used to assess the likelihood of a disturbance profile of the plural disturbance profiles being an anticipated disturbance profile, the anticipated disturbance profile being a disturbance profile that is determined to match with the current patient data based on the probability analysis;

determining an insulin dose amount based on the anticipated disturbance profile, the current patient data, previous insulin dose amount data, and a total daily insulin (TDI) for the patient; and outputting a signal representative of the insulin dose amount to a device configured for monitoring, influencing, and/or administering insulin levels in the patient.

* * * * *